United States Patent
Higgins et al.

(10) Patent No.: US 8,450,336 B2
(45) Date of Patent: May 28, 2013

(54) USE OF D-SERINE DERIVATIVES FOR THE TREATMENT OF ANXIETY DISORDERS

(75) Inventors: Guy Higgins, Toronto (CA); Abdelmalik Slassi, Mississauga (CA); Methvin Isaac, Brampton (CA)

(73) Assignee: NPS Pharmaceuticals, Inc, Bedminster, NJ (US)

( * ) Notice: Subject to any disclaimer, the term of this patent is extended or adjusted under 35 U.S.C. 154(b) by 474 days.

(21) Appl. No.: 12/519,041

(22) PCT Filed: Dec. 14, 2007

(86) PCT No.: PCT/CA2007/002256
§ 371 (c)(1),
(2), (4) Date: Sep. 22, 2009

(87) PCT Pub. No.: WO2008/070994
PCT Pub. Date: Jun. 19, 2008

(65) Prior Publication Data
US 2010/0016403 A1     Jan. 21, 2010

Related U.S. Application Data

(60) Provisional application No. 60/870,008, filed on Dec. 14, 2006.

(51) Int. Cl.
*A61K 31/435* (2006.01)
*A61K 31/385* (2006.01)
*A61K 31/335* (2006.01)

(52) U.S. Cl.
USPC ............ 514/277; 514/439; 514/449

(58) Field of Classification Search
USPC .................... 514/277, 439, 449
See application file for complete search history.

(56) References Cited

U.S. PATENT DOCUMENTS

| | | | |
|---|---|---|---|
| 5,378,729 | A | 1/1995 | Kohn et al. |
| 5,610,162 | A | 3/1997 | Witzel et al. |
| 5,654,301 | A | 8/1997 | Kohn et al. |
| 5,773,475 | A | 6/1998 | Kohn et al. |
| 5,880,158 | A | 3/1999 | Kohn |
| 6,355,799 | B1 | 3/2002 | Gupta et al. |
| 6,362,177 | B1 | 3/2002 | Shiota et al. |
| RE38,551 | E | 7/2004 | Kohn |
| 2001/0041802 | A1 | 11/2001 | Kym et al. |
| 2002/0120011 | A1 | 8/2002 | Sikorski et al. |
| 2002/0156081 | A1 | 10/2002 | Hirst et al. |
| 2005/0131014 | A1 | 6/2005 | Collini et al. |
| 2005/0137243 | A1 | 6/2005 | Souers et al. |
| 2005/0261204 | A1 | 11/2005 | Stohr |
| 2005/0277596 | A1 | 12/2005 | Stohr |
| 2005/0277638 | A1 | 12/2005 | Souers et al. |
| 2005/0288234 | A1 | 12/2005 | Stohr |
| 2006/0009384 | A1 | 1/2006 | Rudd et al. |
| 2006/0100157 | A1 | 5/2006 | Rauschkolb-Loffler et al. |
| 2006/0252749 | A1 | 11/2006 | Stohr |
| 2007/0042969 | A1 | 2/2007 | Rauschkolb-Loffler et al. |
| 2007/0043120 | A1 | 2/2007 | Beyreuther et al. |
| 2007/0048372 | A1 | 3/2007 | Beyreuther et al. |
| 2007/0197657 | A1 | 8/2007 | Beyreuther et al. |
| 2009/0005433 | A1 | 1/2009 | Higgins et al. |

FOREIGN PATENT DOCUMENTS

| | | |
|---|---|---|
| EP | 0592490 | 1/1998 |
| EP | 0649306 | 1/2001 |
| EP | 1464335 | 10/2004 |
| EP | 1920780 | 5/2008 |
| JP | 2005247841 | 9/2005 |
| JP | 2006219408 | 8/2006 |
| JP | 2007091649 | 4/2007 |
| WO | WO 9015069 | 12/1990 |
| WO | WO 9323041 | 11/1993 |
| WO | WO 0000463 | 1/2000 |
| WO | WO 0058346 | 10/2000 |
| WO | WO 0168644 | 9/2001 |
| WO | WO 02074297 | 9/2002 |
| WO | WO 03028720 | 4/2003 |
| WO | WO 03047499 | 6/2003 |
| WO | WO 03072535 | 9/2003 |

(Continued)

OTHER PUBLICATIONS

Vippagunta et al. "Crystalline solids". Advanced Drug Delivery Reviews 48 (2001) 3-26.*
International Preliminary Report on Patentability and Written Opinion issued in International Application No. PCT/US2006/062153 dated Jun. 24, 2008.
International Preliminary Report on Patentability and Written Opinion issued in International Application No. PCT/US2007/002256 dated Jun. 16, 2009.
International Search Report issued in International Application No. PCT/US2006/062153 dated Jan. 6, 2007.
International Search Report issued in International Application No. PCT/US2007/002256 dated Apr. 14, 2008.
Office Action issued in U.S. Appl. No. 11/610,864 dated Apr. 2, 2009.

(Continued)

*Primary Examiner* — Renee Claytor
(74) *Attorney, Agent, or Firm* — Stoel Rives, LLP

(57) ABSTRACT

Compounds of Formula I are useful for the treatment of anxiety disorders such as generalized anxiety disorder (GAD), panic attack, post traumatic stress disorder (PTSD), obsessive compulsive disorder (OCD) and social phobias. wherein: A is chosen from: aryl or heteroaryl, A being optionally substituted with up to 5 independently-selected groups $R^8$; $R^1$ is chosen from: alkyl or haloalkyl; $R^2$ is chosen from: H, $C(O)R^6$, $C(O)OR^6$, $SO2R^6$ or $C(O)NR^6R^7$; $R^3$, $R^4$ and $R^5$ are independently chosen from: H or alkyl; $R^6$ and $R^7$ are independently chosen from: H or alkyl; and $R^8$ is chosen from: OH, CN, halo, alkyl, alkoxy, haloalkyl, haloalkoxy, $C(O)R^6$, $C(O)OR^6$, $SO2R^6$ or $C(O)NR^6R^7$.

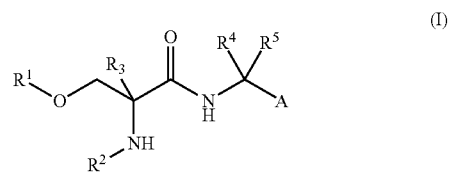

(I)

9 Claims, No Drawings

FOREIGN PATENT DOCUMENTS

| | | |
|---|---|---|
| WO | WO 2004045284 | 6/2004 |
| WO | WO 2004060313 | 7/2004 |
| WO | WO 2004100865 | 11/2004 |
| WO | WO 2005028429 | 3/2005 |
| WO | WO 2005035551 | 4/2005 |
| WO | WO 2005053667 | 6/2005 |
| WO | WO 2005058883 | 6/2005 |
| WO | WO 2005095387 | 10/2005 |
| WO | WO 2005095397 | 10/2005 |
| WO | WO 2005099740 | 10/2005 |
| WO | WO 2005105802 | 11/2005 |
| WO | WO 2005110390 | 11/2005 |
| WO | WO 2005115147 | 12/2005 |
| WO | WO 2006000397 | 1/2006 |
| WO | WO 2006024823 | 3/2006 |
| WO | WO 2006034004 | 3/2006 |
| WO | WO 2006137485 | 12/2006 |
| WO | WO 2007004749 | 1/2007 |
| WO | WO 2007076306 | 7/2007 |
| WO | WO 2007095588 | 8/2007 |
| WO | WO 2008070994 | 6/2008 |

OTHER PUBLICATIONS

West, "Solid State Chemistry and its Applications", Wiley, New York, 1988, 358 & 365.

Eisele, "Sequence Variation on an Antiboiotically Active Tripeptide", Z. Naturforsch. 30c, 541-543, 1975.

Godunova, et al., "Asymmetric Synthesis of Amino Acids Via Catalytic Reduction of Azalactone-Subtituted Acylaminoacrylic Acids", N.D. Zalinskii Institute of Organic Chemistry, translated from: Izvestiya Akademii Nauk SSR, Seriya Khimicheskaya, No. 2, 351-354, 1989.

Kadar, et al., "Effects of Cholecystokinin Octapeptides and Their Fragments on Seizures Induced by Different Convulsive Drugs", Neuropeptides and Psychosomatic Processes, 231-238.

Office Action issued in U.S. Appl. No. 11/610,864 dated Dec. 23, 2009.

Response to Office Action filed in U.S. Appl. No. 11/610,864, filed Oct. 2, 2009.

Request for Continued Examination in U.S. Appl. No. 11/610,864 dated May 24, 2010.

* cited by examiner

USE OF D-SERINE DERIVATIVES FOR THE TREATMENT OF ANXIETY DISORDERS

TECHNICAL FIELD

The present disclosure relates the use serine derivatives, to processes for their preparation, to pharmaceutical compositions containing them, and to their usefulness in the treatment of anxiety disorders.

BACKGROUND

Anxiety is broadly defined as a state of unwarranted or inappropriate worry often accompanied by restlessness, tension, distraction, irritability and sleep disturbances. This disproportionate response to environmental stimuli can hyperactivate the hypothalamic-pituitary-adrenal axis and the autonomic nervous system, resulting in somatic manifestation of anxiety, including shortness of breath, sweating, nausea, rapid heartbeat and elevated blood pressure (Sanford et al. *Pharmacol. Ther.* 2000, 88: 197-212). Anxiety disorders represent a range of conditions and as a result have been classified into multiple distinct conditions, including generalized anxiety disorder (GAD), panic attack, post traumatic stress disorder (PTSD), obsessive compulsive disorder (OCD) and social phobias (Sanford et al. *Acta. Psychiatr. Scand. Suppl.* 1998, 393: 74-80).

Generalized anxiety disorder (GAD) is the most common of the anxiety disorders that is characterized by excessive and persistent worries. In the general population the lifetime prevalence rate of GAD range from 4.1 to 6.6% with somewhat higher rates in woman than in man. The individual with GAD worries about life events such as marital relationships, job performance, health, money and social status. Individuals with GAD startle easily and may suffer from depression. Some of the specific symptoms of GAD include restlessness, motor tension, difficulty concentrating, irritability, and sleep disturbances. The severity of the symptoms over time may be linked to the changing nature of the environmental stressor. With increasing age, GAD symptoms become less severe.

Panic Disorder is a well-studied psychiatric condition that consists of multiple disabling panic attacks characterized by and intense autonomic arousal. In addition, heightened fear and anxiety states occur both during and between panic attacks. Approximately 3% of woman and 1.5% of men have panic attacks. During a panic attack, the individual experiences multiple symptoms including light-headedness, a pounding heart and difficulty in breathing. Panic disorder may be caused by an oversensitive brain system regulating autonomic functions. Potential brain regions involved in panic attack are the locus ceruleus, hippocampus and amygdala. Pathophysiology in the brain GABA-benzodiazepine receptor system may also contribute to the production of panic attack.

Post traumatic stress disorder (PTSD) is another example of a disorder associated with intense fear and anxiety states that require psychiatric treatment. PTSD results from exposure to a life threatening or traumatic event. Individuals with PTSD have recurring thoughts of the terrifying event. Reenactment of the event varies in duration from a few seconds or hours to several days. Individuals with major depression, with panic disorders or lacking strong social supports are vulnerable to develop PTSD Anxiety disorders, which occur in 10% to 30% of the population, represent not only a significant public health issue but place a substantial economic burden on society. A number of drugs have either been developed or are being developed for treating the different subclasses of anxiety. Some of these agents such as tricyclic antidepressants and b-adrenoreceptor antagonists found either limited use in treating specific disorders such as performance anxiety (e.g., b-adrenoreceptor antagonists suppression of the sympathetic manifestations of anxiety) or have fallen out of favor for reasons of efficacy and/or safety. Currently, direct and indirect serotonin receptor agonists [e.g., selective serotonin reuptake inhibitors (SSRI) and buspirone] and benzodiazepines are most often prescribed for treating anxiety disorders with benzodiazepine receptor agonist being a preferred therapeutic modality. See Atack et al. *Curr. Drug Targets. CNS. Neurol. Disord.* 2003, 2: 213-232; Stahl et al. *J. Clin. Psychiatry* 2002, 63: 756-757; Uhlenhuth et al. *J. Clin. Psychopharmacol.* 1999, 19: 23S-24S; Varia et al. *Int. Clin. Psychopharmacol.* 2002, 17: 103-107; Vaswani et al. *Prog. Neuropsychopharmacol. Biol. Psychiatry* 2003, 27: 85-102. The ability of benzodiazepines to enhance g-aminobutyric acid (GABA) neurotransmission safely and rapidly is central to their effectiveness in treating anxiety disorder, especially GAD and panic disorders (Stahl et al. *J. Clin. Psychiatry* 2002, 63: 756-757). Benzodiazepines act by positively modulating the inhibitory neurotransmitter GABA through an allosteric site on the GABA A receptor complex, a ligand-gated chloride ion channel. Nonetheless, the use of benzodiazepines is limited by side effects associated with enhanced GABAergic neurotransmission, manifesting as sedation, muscle relaxation, amnesia and ataxia. Moreover, the potential for abuse and physical dependence is associated with the long-term use of benzodiazepines. Furthermore, some forms of anxiety such as OCD are relatively resistant to benzodiazepine treatment. These therapeutic limitations and the societal burdens of anxiety provide the impetus for the development of novel anxiolytics or anxioselective agents.

The concept of anxioselectivity is used to describe anxiolysis in the absence of side effects typically associated with benzodiazepines. This search for alternative strategies to treat anxiety disorders have led to the growing use of SSRIs, in addition to a number of other molecular targets including metabotropic glutamate receptors (mGluRs) that are currently under evaluation (Schoepp et al *Nat. Rev. Drug Dis.* 2005, 4 (2): 131-144. However, none of the alternative targets has been shown to match either the efficacy or rapid onset of benzodiazepine.

The present invention is directed to the D-serine analogs for the treatment of anxiety disorders such as generalized anxiety disorder (GAD), panic attack, post traumatic stress disorder (PTSD), obsessive compulsive disorder (OCD) and social phobias.

It has now been found that compounds of Formula I are useful in the treatment of anxiety related disorders such as those denoted above.

SUMMARY

We have discovered that compounds of Formula I:

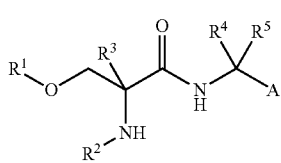

Formula I wherein:
A is chosen from: aryl or heteroaryl, A being optionally substituted with up to 5 independently-selected groups $R^8$;
$R^1$ is chosen from: alkyl or haloalkyl;
$R^2$ is chosen from: H, C(O)$R^6$, C(O)O$R^6$, SO$_2R^6$ or C(O)N$R^6R^7$;
$R^3$, $R^4$ and $R^5$ are independently chosen from: H or alkyl;
$R^6$ and $R^7$ are independently chosen from: H or alkyl; and
$R^8$ is chosen from: OH, CN, halo, alkyl, alkoxy, haloalkyl, haloalkoxy, C(O)$R^6$, C(O)O$R^6$, SO$_2R^6$ or C(O)N$R^6R^7$;
are useful in the treatment of anxiety disorders such as generalized anxiety disorder (GAD), panic attack, post traumatic stress disorder (PTSD), obsessive compulsive disorder (OCD) and social phobias.

In another aspect of the disclosure compositions are provided containing the present compounds in amounts for pharmaceutical use to treat medical conditions such as anxiety disorders such as generalized anxiety disorder (GAD), panic attack, post traumatic stress disorder (PTSD), obsessive compulsive disorder (OCD) and social phobias; such compositions comprise a compound of Formula I in association with one or more pharmaceutically acceptable diluents, excipients and/or inert carriers.

DEFINITIONS

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

The term "alkyl" as used herein means a straight- or branched-chain hydrocarbon radical having from one to six carbon atoms, and includes methyl, ethyl, propyl, isopropyl, t-butyl and the like.

The term "alkoxy" as used herein means a straight- or branched-chain alkoxy radical having from one to six carbon atoms and includes methoxy, ethoxy, propyloxy, isopropyloxy, t-butoxy and the like.

The term "halo" as used herein means halogen and includes fluoro, chloro, bromo, iodo and the like, in both radioactive and non-radioactive forms.

The term "haloalkyl" as used herein means an alkyl group in which at least one H atom has been replaced by a halo atom, and includes groups such as CF$_3$, CH$_2$Br and the like.

The term "haloalkoxy" as used herein means an alkoxy group in which at least one H atom has been replaced by a halo atom, and includes groups such as OCF$_3$, OCH$_2$Br and the like.

The term "aryl" as used herein means an aromatic group having five to twelve atoms, and includes phenyl, naphthyl and the like.

The term "heteroaryl" means an aromatic group which includes at least one heteroatom selected from at least one of the following: N, S and O, and includes groups and includes pyridyl, indolyl, furyl, benzofuryl, thienyl, benzothienyl, quinolyl, oxazolyl and the like.

DETAILED DESCRIPTION

One embodiment of the disclosure provides compounds of Formula I, or a salt or solvate thereof, for the treatment of anxiety disorders such as generalized anxiety disorder (GAD), panic attack, post traumatic stress disorder (PTSD), obsessive compulsive disorder (OCD) and social phobias.

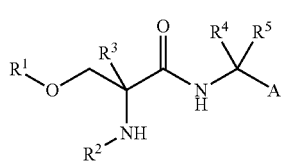

Formula I wherein:
A is chosen from: aryl or heteroaryl, optionally substituted with up to 5 independently-selected groups $R^8$;
$R^1$ is chosen from: alkyl or haloalkyl;
$R^2$ is chosen from: C(O)$R^6$, C(O)O$R^6$, SO$_2R^6$ or C(O)N$R^6R^7$;
$R^3$, $R^4$ and $R^5$ are independently chosen from: H or alkyl;
$R^6$ and $R^7$ are independently chosen from: H or alkyl; and
$R^8$ is chosen from: OH, CN, halo, alkyl, alkoxy, haloalkyl, haloalkoxy, C(O)$R^6$, C(O)O$R^6$, SO$_2R^6$ or C(O)N$R^6R^7$.

Another embodiment provides compounds of Formula I in which $R^1$ is a haloalkyl group, or a salt or solvate thereof for the treatment of anxiety disorders such as generalized anxiety disorder (GAD), panic attack, post traumatic stress disorder (PTSD), obsessive compulsive disorder (OCD) and social phobias.

The introduction of the haloalkyl group ($R^1$) in compounds of Formula I brings about dramatic changes in the physical and chemical properties of the molecules as compared to the analogous parent alkyl compounds, and can result in the enhancement of pharmacokinetic properties and biological activities. The unique properties of the fluorine atom include it small size, low polarizability, high electronegativity and its ability to form strong bonds with carbon. Recently, bioactive compounds containing trifluoromethoxy, difluoromethoxy and fluoromethoxy groups have attracted great interest. Replacement of hydrogen atoms can sometimes result in improved thermal and metabolic stability. Improved metabolic stability is usually a desirable feature since the possibility exists that in vivo decomposition may produce toxic effects.

The geminal combination of an alkoxyl or aryloxy group with a fluorine atom offers the possibility of bonding/non-bonding resonance, which can be formally expressed by the superposition of a covalent and ionic limiting structure. This phenomenon, which reveals itself as a lengthening and weakening of the carbon-halogen bond and a shortening and strengthening of the carbon-oxygen bond is widely known as the generalized anomeric effect [Schlosser et al *Chem. Rev.* 2005, 105: 827-856].

Exemplary compounds useful in the practice of the invention include, but is not limited to:
2-Amino-N-benzyl-3-(difluoromethoxy)propanamide,
2-Amino-3-difluoromethoxy-N-(4-fluorobenzyl)propionamide,
2-(Acetylamino)-N-benzyl-3-(difluoro-methoxy)propanamide,
2-(Acetylamino)-3-(difluoromethoxy)-N-(4-fluoro-benzyl)propanamide,
2-(Acetylamino)-N-(3,4-difluorobenzyl)-3-(difluoromethoxy)propanamide,
tert-Butyl {(1R)-2-(benzylamino)-1-[(difluoromethoxy)methyl]-2-oxoethyl}carbamate,
tert-Butyl {(1R)-1-[(difluoromethoxy)methyl]-2-[(4-fluorobenzyl)amino]-2-oxoethyl}carbamate, (2R)-2-(Acetylamino)-N-benzyl-3-(difluoro-methoxy)propanamide, tert-butyl {(1R)-1-[(difluoromethoxy)methyl]-2-[(3-fluorobenzyl amino]-2-oxoethyl}carbamate, tert-butyl {(1R)-1-[(difluoromethoxy)methyl]-2-[(3,4-difluorobenzyl)amino]-2-oxoethyl}carbamate, Tert-butyl {(1R)-1-[(difluoromethoxy)methyl]-2-oxo-2-[(2-thienylmethyl)amino]ethyl}carbamate, tert-butyl {(1R)-1-[(difluoromethoxy)methyl]-2-[(4-methylbenzyl)amino]-2-oxoethyl}carbamate, tert-butyl {(1R)-2-[(3-chlorobenzyl)amino]-1-[(difluoromethoxy)methyl]-2-oxoethyl}carbamate, tert-butyl {(1R)-2-[(3-methylbenzyl)amino]-1-[(difluoromethoxy)methyl]-2-oxoethyl}carbamate, tert-butyl {(1R)-1-[(difluoromethoxy)methyl]-2-oxo-2-[(3-thienylmethyl)amino]ethyl}carbamate, (2R)-2-(Acetylamino)-3-(difluoromethoxy)-N-(4-fluorobenzyl)propanamide, (2R)—N-benzyl-3-(difluoromethoxy)-2-[(methylsulfonyl)amino]propanamide, (2R)-3-(difluoromethoxy)-N-(4-fluorobenzyl)-2[(methylsulfonyl)amino]propanamide, (2R)-2-(acetylamino)-N-(4-chlorobenzyl)-3-(difluoromethoxy)propanamide, (2R)-2-(acetylamino)-3-(difluoromethoxy)-N-(3-fluorobenzyl)propanamide, (2R)-2-(acetylamino)-N-(3,4-difluorobenzyl)-3-(difluoromethoxy)propanamide, (2R)-2-(acetylamino)-3-(difluoromethoxy)-N-(2-thienylmethyl)propanamide, (2R)-2-(acetylamino)-3-(difluoromethoxy)-N-(4-methylbenzyl)propanamide, (2R)-2-(acetylamino)-N-(3-chlorobenzyl)-3-(difluoromethoxy)propanamide, (2R)-2-(acetylamino)-3-(difluoromethoxy)-N-(3-methylbenzyl)propanamide, (2R)-2-(acetylamino)-3-(difluoromethoxy)-N-(3-thienylmethyl)propanamide, 2-Acetylamino-N-benzyl-3-difluoromethoxy-propionamide, 2-Acetylamino-3-difluoromethoxy-N-(4-fluoro-benzyl)-propionamide, 2-Acetylamino-N-(3,4-difluoro-benzyl)-3-difluoromethoxy-propionamide; and lacosamide((+)-(2R)-2-(acetylamino)-N-benzyl-3-methoxypropanamide).

Preparation of Compounds of Formula I.

WO 97/33861 discloses related compounds in which $R^1$ is alkyl, such as lacosamide:

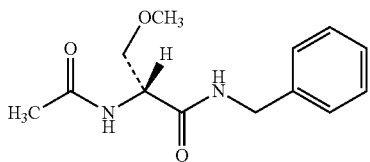 [SMILES: COC[C@@H](NC(C)=O)C(=O)NCc1ccccc1]

Compounds of Formula I in which $R^1$ is haloalkyl may be prepared as shown below.

Fluoro methyl ether derivatives [Manson et al *J. Am. Chem. Soc.* 1956, 78: 1682] can be obtained from the corresponding chloro analogs by nucleophilic substitution with KF. Chloromethylethers are readily accessible [Hayashi et al *Bull. Chem. Soc. Jpn* 1980, 53: 2701; Marvel et al *Org. Syn. Coll. Vol.* 1941, 1: 369; Davis et al *Org. Synth.* 1967, 47: 123.; Sharma et al *J. Org. Chem.* 1968, 33: 3335.; Hayami et al *Bull. Chem. Soc. Jpn* 1971, 44: 3091]. The O-α-fluoro alkyl ethers can be most conveniently prepared from the reaction of the vinyl ether with N-Bromosuccinimide (NBS) in the presence of HF followed by reductive debromination.

O-α-fluoro alkyl ethers

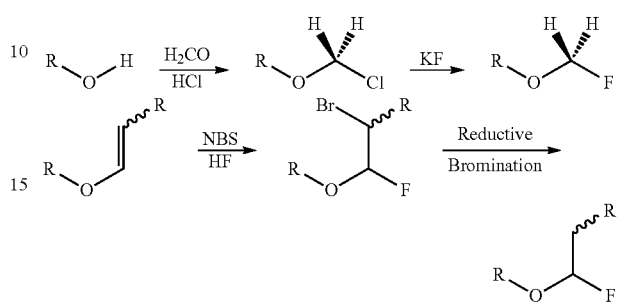

The O-α,α-difluoro alkyl ethers can be prepared by electrophilic reactions of the appropriate alkoxide anion with Chlorodifluoromethylation in the presence of base [Clark et al *J. Am. Chem. Soc.* 1955, 77: 6618; Miller et al *J. Org. Chem.* 1960, 25: 2009, Sharma et al *J. Fluorine. Chem.* 1988, 41: 247]; difluorocarbene [Naumann et al *J. Fluorine. Chem.* 1994, 67: 91; Naumann et al *Liebigs. Ann.* 1995, 1717-1719] and difluoromethylcarbocation equivalent [Uneyama et al *Tetrahedron Lett.* 1993, 34: 1311; Uneyama et al *J. Org. Chem.* 1995, 60:370;].

Alternatively, the difluoromethyl ethers could also be accessible by sulfur tetrafluoride mediated fluorodeoxygenation of formates [Sheppard et al *J. Org. Chem.* 1964, 29: 1], or from the treatment of the alcohol with Iododifluoromethyl phenyl sulphone to give the corresponding ether which can undergo reductive desulphonylation [Olah et al *Org. Lett.* 2005, 6: 4315].

O-α,α-difluoro alkyl ethers

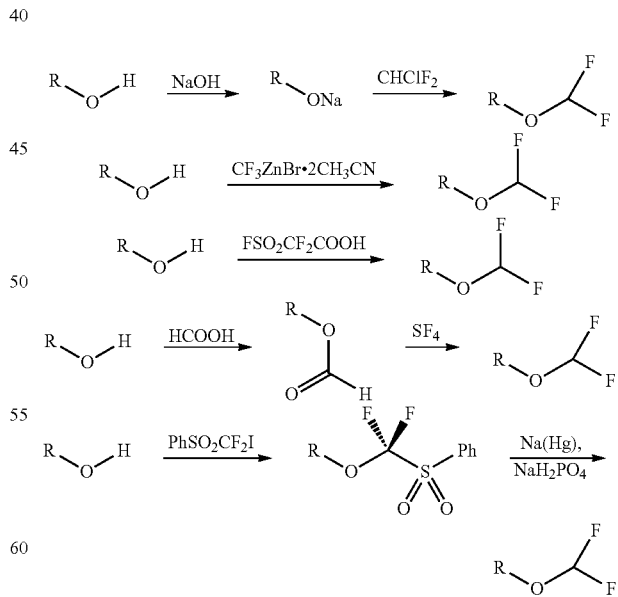

The O-α,α,α-trifluoro alkyl ethers can be prepared by a recently disclosed fluorodesulfurization involving the treatment of dithiocarbonates (xanthogenates) with excess HF/Pyridine and 1,3-dibromo-5,5-dimethylhydantoin. The trifluoromethyl ethers are usually formed in moderate to excellent yield [Kanie et al *Bull. Chem. Soc. Jpn* 2000, 73: 471; Kanie et al *Adv. Synth. Catal.* 2001, 343: 235].

O-α,α,α-trifluoro alkyl ethers

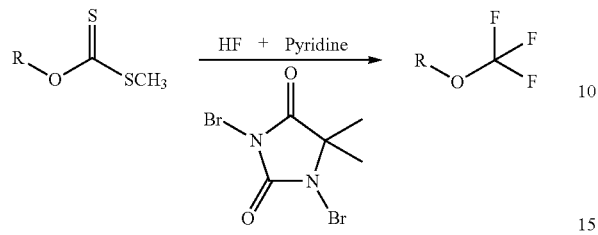

Alkyl trifluoromethyl ethers can also be prepared by (1) treating alkyfluoroformates with SF4 [Sheppard et al *J. Org. Chem.* 1964, 29: 11]; (2) trifluoromethyl transfer from O-(trifluoromethyl) dibenzofuranium tetrafluoroborate [Umemoto, T. *Chem. Rew.* 1996, 96: 1757] and (3) the addition of trifluoromethyl hypofluorite (FOCF3) to alkenes [Rozen, S. *Chem. Rew.* 1996, 96: 1717].

As referred to above, individual compounds of Formula II below, may be prepared according to various methods described above utilizing the appropriately protected series as the representative alcohol precursor.

Synthesis of Difluoromethoxy Compounds

A compound of Formula I wherein $R^1$ is lower alkyl, $CHF_2$, $CFH_2$ or halogenated alkyl, and A is aryl, substituted aryl, alkyl or heteroaryl etc. can be prepared as shown in Scheme 1, below.

The commercially available amino acid serine 1 ($R^3$=H) can first be N-protected with G1 and G2 (e.g. G1=G2 is Benzyl) to provide N,N-dibenzylamino intermediate 2, which then can be easily transformed into the ester precursor 3 (benzyl ester derivative shown). The corresponding benzyl-ester 3 can be converted to the difluoromethoxy derivative utilizing difluoromethylating agents such as $FSO_2CF_2COOH$ or $CF_3ZnBr.2CH_3CN$, followed by deprotection conditions (e.g. shown is hydrogenation) to afford the difluoromethoxy-serine precursor 4. Acylation of 4, utilizing procedures established in the art with $Boc_2O$ or $Ac_2O$ among others to give intermediate 5, which was subjected to amide bond formation using known coupling procedures, provides the difluoromethoxy derivatives of Formula II.

Scheme 1

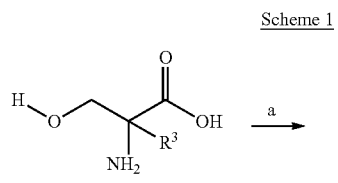

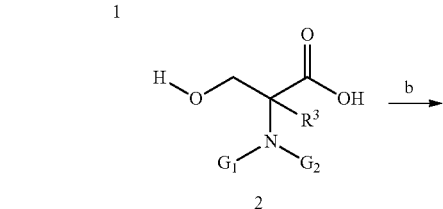

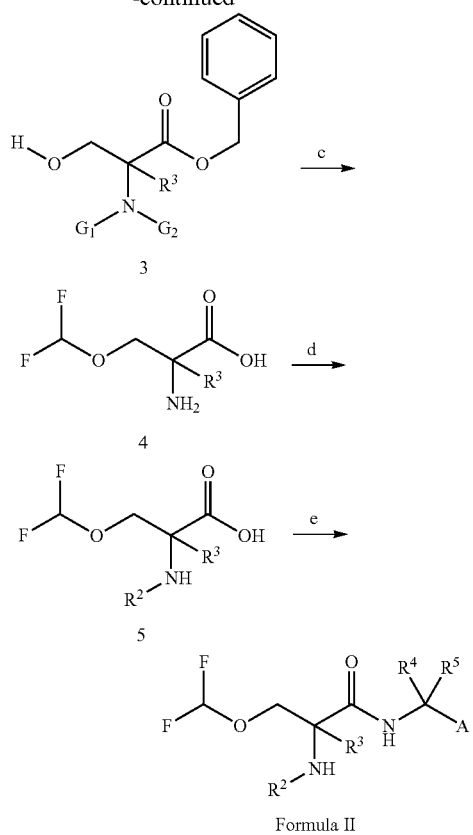

Formula II a) $PhCH_2Br$ (2 eq), $K_2CO_3$, $CH_3CN$;
b) $PhCH_2Br$, $K_2CO_3$, $CH_3CN$
c) i. $FSO_2CF_2COOH$, $Na_2SO_4$, $CH_3CN$ or $CF_3ZnBr\cdot 2CH_3CN/CH_2Cl_2$; ii. $H_2$, Pd, solvent;
d) $Boc_2O$ or $Ac_2O$ ($R^2$ = Boc or Ac)
e) i. $ClCOOCH_2CH(CH_3)_2$, $Et_3N$, THF ii. $ACR^4R^5NH_2$ An alternative synthesis of compound of Formula II wherein $R^1$ is $CHF_2$ utilizes the difluoro (phenylseleno)-methylcarbocation equivalent (obtained via a Pummerer rearrangement of difluoromethyl phenyl selenoxide) and the cyclic ether oxetane. The reaction of difluoromethyl phenyl selenoxide 6 [Uneyama et al *Tetrahedron Lett.* 1993, 34: 1311; Uneyama et al *J. Org. Chem.* 1995, 60: 370;] with oxetane 7 in acetic anhydride should give the intermediate 8 which can undergo reductive deselenation to afford 9. Hydrolysis of 9 followed by oxidation should provide the difluoromethoxy acid 10. Activation of acid 10 should give the oxazolidinones 11, which undergoes α-azidation to afford 11. Staudinger reduction of 11 and subsequent acetylation with acetic anhydride should give 12. Treatment of 12 with the amine should provide the difluoromethoxy derivatives of Formula II, as shown in Scheme 2, below.

Scheme 2

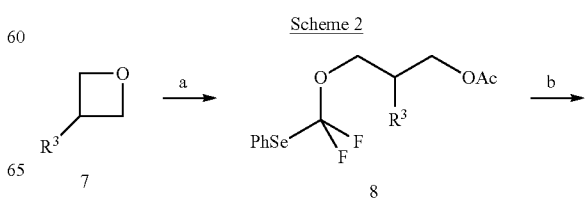

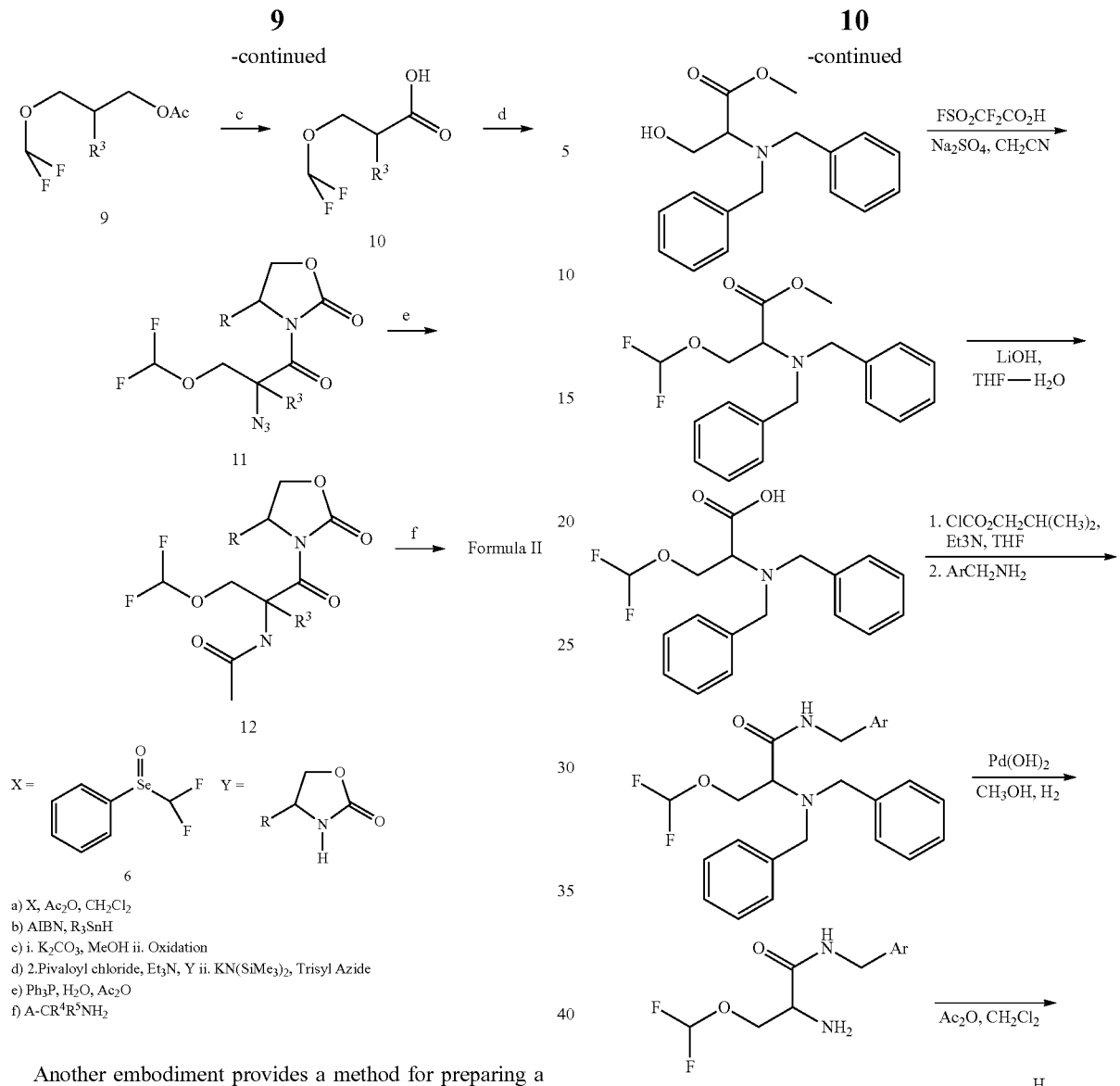
a) X, Ac₂O, CH₂Cl₂
b) AIBN, R₃SnH
c) i. K₂CO₃, MeOH ii. Oxidation
d) 2.Pivaloyl chloride, Et₃N, Y ii. KN(SiMe₃)₂, Trisyl Azide
e) Ph₃P, H₂O, Ac₂O
f) A-CR⁴R⁵NH₂
Another embodiment provides a method for preparing a compound according to Scheme 3, below:
Scheme 3
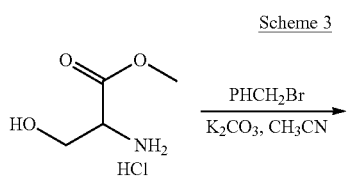
A further embodiment provides a method for preparing a compound according to Scheme 4, below:
Scheme 4
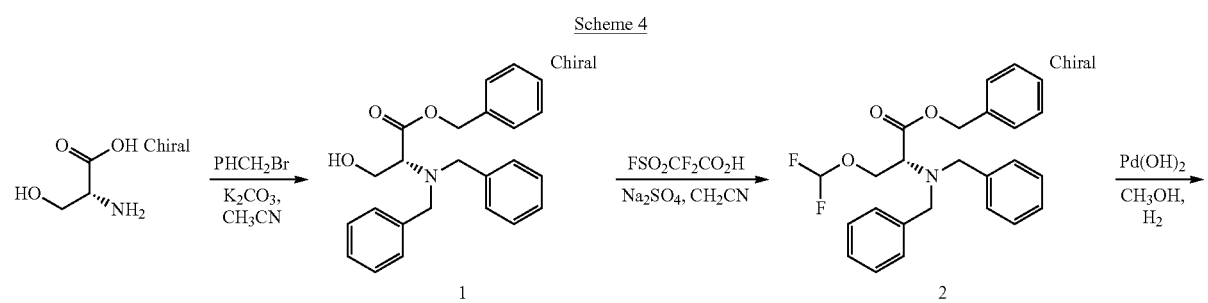

-continued

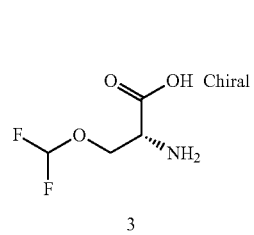
3

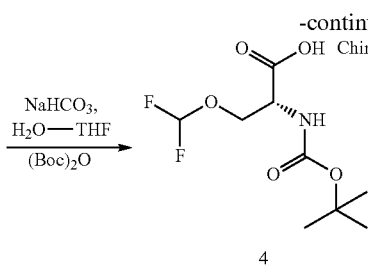
4

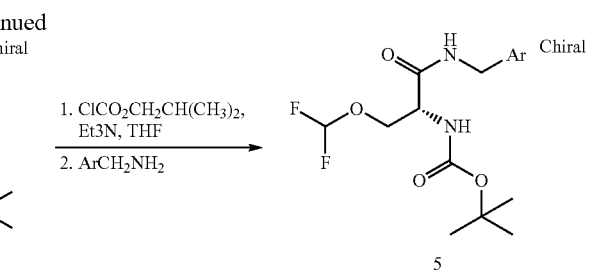
5

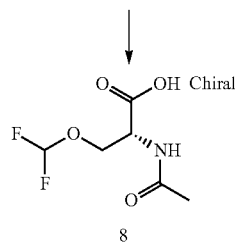
8

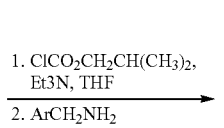
7

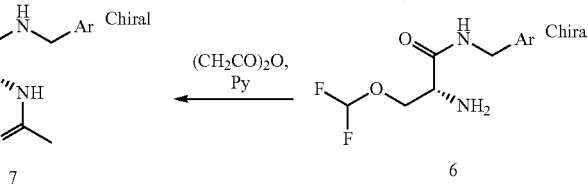
6

For pharmaceutical use, the compounds disclosed are, for instance, administered orally, sublingually, rectally, nasally, vaginally, topically (including the use of a patch or other transdermal delivery device), by pulmonary route by use of an aerosol, or parenterally, including, for example, intramuscularly, subcutaneously, intraperitoneally, intra-arterially, intravenously or intrathecally. Administration can be by means of a pump for periodic or continuous delivery. The compounds disclosed are administered alone, or are combined with a pharmaceutically-acceptable carrier or excipient according to standard pharmaceutical practice. For the oral mode of administration, the compounds disclosed are used in the form of tablets, capsules, lozenges, chewing gum, troches, powders, syrups, elixirs, aqueous solutions and suspensions, and the like. In the case of tablets, carriers that are used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the compounds of the invention are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. For pulmonary administration, diluents and/or carriers will be selected to be appropriate to allow the formation of an aerosol.

Suppository forms of the compounds disclosed are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycols of various molecular weight and fatty acid esters of polyethylene glycol. See, Remington's Pharmaceutical Sciences, 16th Ed., Mack Publishing, Easton, Pa., 1980, pp. 1530-1533 for further discussion of suppository dosage forms. Analogous gels or creams can be used for vaginal, urethral and rectal administrations.

Numerous administration vehicles will be apparent to those of ordinary skill in the art, including without limitation slow release formulations, liposomal formulations and polymeric matrices.

Examples of pharmaceutically acceptable acid addition salts for use with the compounds disclosed include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic and arylsulphonic acids, for example. Examples of pharmaceutically acceptable base addition salts for use with the compounds disclosed include those derived from non-toxic metals such as sodium or potassium, ammonium salts and organoamino salts such as triethylamine salts. Numerous appropriate such salts will be known to those of ordinary skill.

The physician or other health care professional can select the appropriate dose and treatment regimen based on the subject's weight, age, and physical condition. Dosages will generally be selected to maintain a serum level of compounds of the invention between about 0.01 µg/cc and about 1000 µg/cc, preferably between about 0.1 µg/cc and about 100 µg/cc. For parenteral administration, an alternative measure of an exemplary amount is from about 0.001 mg/kg to about 10 mg/kg (alternatively, from about 0.01 mg/kg to about 10 mg/kg), such as from about 0.01 mg/kg to about 1 mg/kg (from about 0.1 mg/kg to about 1 mg/kg), will be administered. For oral administrations, an alternative measure of administration amount is from about 0.001 mg/kg to about 10 mg/kg (from about 0.1 mg/kg to about 10 mg/kg), such as from about 0.01 mg/kg to about 1 mg/kg (from about 0.1 mg/kg to about 1 mg/kg). For administrations in suppository form, an alternative measure of administration amount is from about 0.1 mg/kg to about 10 mg/kg, such as from about 0.1 mg/kg to about 1 mg/kg.

EXAMPLES

All starting materials are commercially available or earlier described in the literature.

The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet). Unless otherwise indicated, in the tables below $^1$H NMR data was obtained at 300 MHz, using CDCl$_3$ as the solvent.

Purification of products were also done using Chem Elut Extraction Columns (Varian, cat #1219-8002), Mega BE-SI (Bond Elut Silica) SPE Columns (Varian, cat #12256018; 12256026; 12256034), or by flash chromatography in silica-filled glass columns.

Example 1.1

Methyl 2-(dibenzylamino)-3-hydroxypropanoate

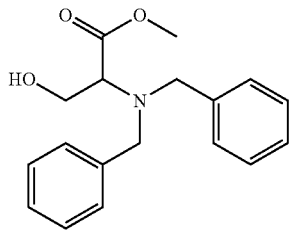 [SMILES: COC(=O)C(CO)N(Cc1ccccc1)Cc1ccccc1]

Methyl serine hydrochloride (15 g, 0.096 mol) was stirred with potassium carbonate (66.6 g, 0.482 mol) and benzyl bromide (41.2 g, 0.24 mol) in acetonitrile (240 mL) at room temperature for 24 hours. The reaction mixture was filtered and washed with ethyl acetate. The filtrate was concentrated with silica gel. The product was purified by column chromatography, eluting with 5-20% ethyl acetate in hexanes, to give methyl 2-(dibenzylamino)-3-hydroxypropanoate (27 g, 93.5%) as a pale-yellow sticky oil. $^1$H NMR (300 MHz, CDCl$_3$): δ(ppm) 7.25-7.40 (m, 10H), 3.94 (d, 2H), 3.83 (s, 3H), 3.79 (m, 2H), 3.71 (d, 2H), 3.60 (t, 1H) and 2.62 (t, 1H).

Example 2.1

Methyl 2-dibenzylamino-3-difluoromethoxy-propionate

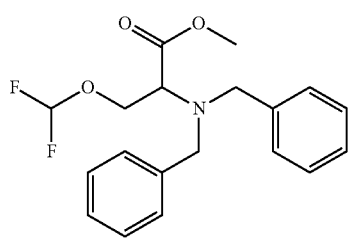 [SMILES: COC(=O)C(COC(F)F)N(Cc1ccccc1)Cc1ccccc1]

To an acetonitrile solution of methyl 2-(dibenzylamino)-3-hydroxypropanoate (23 g, 76.8 mmol) and sodium sulfate (3.9 g, 27.4 mmol) at 40° C., difluoro(fluorosulfonyl)acetic acid (25 g, 140 mmol) was added dropwise for 1.5 hrs. The reaction mixture was concentrated to dryness and the residue was mixed with silica gel in ethyl acetate, then again concentrated to dryness. The product was purified by column chromatography, eluting with 3-4% ethyl acetate in hexanes, to give methyl 2-dibenzylamino-3-difluoromethoxy-propionate (1.3 g, 4.8%) as a colorless oil. $^1$H NMR (300 MHz, CDCl$_3$): δ(ppm) 7.20-7.40 (m, 10H), 6.18 (bt, 1H), 4.05-4.24 (m, 2H), 3.90 (d, 2H), 3.83 (s, 3H) and 3.64-3.71 (m, 3H).

Example 3.1

2-(Dibenzylamino)-3-(difluoromethoxy)propanoic acid

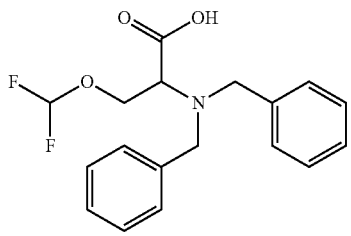 [SMILES: O=C(O)C(COC(F)F)N(Cc1ccccc1)Cc1ccccc1]

Methyl 2-dibenzylamino-3-difluoromethoxy-propionate (1.2 g, 3.43 mmol) was stirred with 1N LiOH (10.3 mL, 10.3 mmol) in THF (40 mL) at 50° C. for 2 hours and then stirred at room temperature overnight. The reaction mixture was diluted with ethyl acetate and acidified with 1N HCl. The organic layer was dried with sodium sulfate and concentrated with silica gel. The product was purified by column chromatography, eluting with 10-50% ethyl acetate in hexanes, to give 2-(dibenzylamino)-3-(difluoromethoxy)propanoic acid (730 mg, 63.5%) as a white solid. $^1$H NMR (300 MHz, CDCl$_3$): δ (ppm) 7.26-7.42 (m, 10H), 6.29 (bt, 1H), 4.45 (dd, 1H), 4.28 (dd, 1H), 3.94 (q, 4H) and 3.85 (m, 1H).

Example 4.1

2-(Dibenzylamino)-3-(difluoromethoxy)-N-benzyl-propanamide

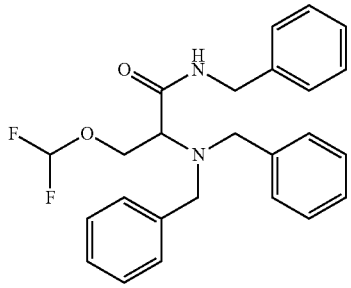 [SMILES: O=C(NCc1ccccc1)C(COC(F)F)N(Cc1ccccc1)Cc1ccccc1]

To a solution of 2-(dibenzylamino)-3-(difluoromethoxy) propanoic acid (335.4 mg, 1 mmol) and triethylamine (404.8 mg, 4 mmol) in THF (5 mL) at −5° C., isobutyl chloroformate (143.5 mg, 1.05 mmol) was added dropwise. After 20 minutes, benzylamine hydrochloride (215.4 mg, 1.5 mmol) was added and the reaction mixture was allowed to warm up to room temperature. The mixture was then diluted with ethyl acetate and washed with water, 0.5N HCl and Brine. The organic layer was dried over magnesium sulphate, concentrated with silica gel and purified by column chromatography, eluting with 10-20% ethyl acetate in hexanes to give 2-(dibenzylamino)-3-(difluoromethoxy)-N-benzylpropanamide (367 mg, 86.5%) as a white solid. $^1$H NMR (300 MHz, CDCl$_3$): δ(ppm) 7.56 (t, 1H), 7.17-7.34 (m, 15H), 6.35 (wt, 1H), 4.60 (dd, 1H), 4.43 (m, 3H), 3.95 (d, 2H), 3.68 (d, 2H) and 3.67 (m, 1H).

Example 5.1

2-Dibenzylamino-3-difluoromethoxy-N-(4-fluorobenzyl)propionamide

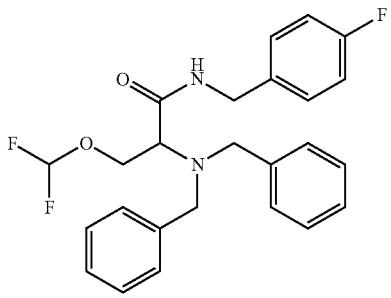 [SMILES: O=C(NCc1ccc(F)cc1)C(COC(F)F)N(Cc1ccccc1)Cc1ccccc1]

To a solution of 2-(dibenzylamino)-3-(difluoromethoxy) propanoic acid (335.4 mg, 1 mmol) and triethylamine (404.8 mg, 4 mmol) in THF (5 mL) at −5° C., isobutyl chloroformate (143.5 mg, 1.05 mmol) was added dropwise. After 20 minutes, 4-fluorobenzylamine (137.5 mg, 1.1 mmol) was added and the reaction mixture was allowed to warm up to room temperature. The mixture then was diluted with ethyl acetate and washed with water, 0.5 N HCl and Brine. The organic layer was dried over magnesium sulphate, concentrated with silica gel and purified by column chromatography, eluting with 10-20% ethyl acetate in hexanes, to give 2-dibenzylamino-3-difluoromethoxy-N-(4-fluorobenzyl)propionamide (395 mg, 89.2%) as a colorless oil. $^1$H NMR (300 MHz, CDCl$_3$): δ (ppm) 7.56 (t, 1H), 6.98-7.32 (m, 14H), 6.35 (wt, 1H), 4.61 (dd, 1H), 4.41 (m, 3H), 3.86 (d, 2H), 3.70 (d, 2H) and 3.68 (m, 1H).

Example 6.1

2-Dibenzylamino-N-(3,4-difluoro-benzyl)-3-difluoromethoxy-propion-amide

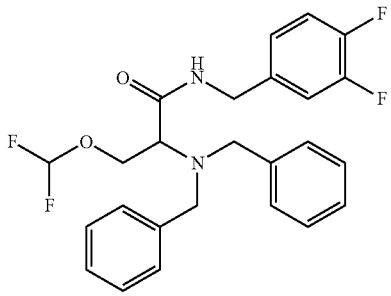 [SMILES: O=C(NCc1ccc(F)c(F)c1)C(COC(F)F)N(Cc1ccccc1)Cc1ccccc1]

To a solution of 2-(dibenzylamino)-3-(difluoromethoxy) propanoic acid (280 mg, 0.835 mmol) and triethylamine (338 mg, 3.34 mmol) in THF (5 mL) at −5° C., isobutyl chloroformate (119.8 mg, 0.876 mmol) was added dropwise. After 20 minutes, 3,4-difluorobenzylamine (131.3 mg, 0.919 mmol) was added and the reaction mixture allowed to warm up to 0° C. for another hour. The mixture was then diluted with ethyl acetate and washed with water, 0.5 N HCl and Brine. The organic layer was dried over magnesium sulphate, concentrated with silica gel and purified by column chromatography, eluting with 10~20% ethyl acetate in hexanes, to give 2-dibenzylamino-N-(3,4-difluoro-benzyl)-3-difluoromethoxy-propionamide (298 mg, 77.5%) as a colorless oil. $^1$H NMR (300 MHz, CDCl$_3$): δ(ppm) 7.56 (t, 1H), 6.82-7.38 (m, 13H), 6.60 (wt, 1H), 4.58 (dd, 1H), 4.37 (m, 3H), 3.90 (d, 2H), 3.73 (d, 2H) and 3.70 (m, 1H).

Example 7.1

2-Amino-N-benzyl-3-(difluoromethoxy)propanamide

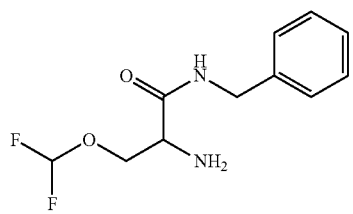 [SMILES: NC(COC(F)F)C(=O)NCc1ccccc1]

2-(Dibenzylamino)-3-(difluoromethoxy)-N-benzylpropanamide (362 mg, 0.863 mmol) was stirred with 10% Pd(OH)$_2$ (200 mg) in ethanol under H$_2$ overnight. The reaction mixture was filtered and concentrated to give 2-amino-N-benzyl-3-(difluoromethoxy)propanamide (195 mg, 93.6%) as a colorless oil. $^1$H NMR (300 MHz, CDCl$_3$): δ(ppm) 7.83 (t, 1H), 7.25-7.40 (m, 5H), 6.27 (wt, 1H), 4.49 (d, 2H), 4.19 (d, 2H) and 3.68 (m, 1H).

Example 8.1

2-Amino-3-difluoromethoxy-N-(4-fluorobenzyl) propionamide

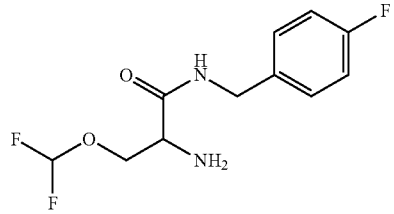 [SMILES: NC(COC(F)F)C(=O)NCc1ccc(F)cc1]

2-Dibenzylamino-3-difluoromethoxy-N-(4-fluorobenzyl) propionamide (390 mg, 0.881 mmol) was stirred with 10% Pd(OH)$_2$ (200 mg) in ethanol under H$_2$ overnight. The reaction mixture was filtered and concentrated to give 2-mino-3-difluoromethoxy-N-(4-fluorobenzyl)propionamide (200 mg, 86.5%) as a colorless oil. $^1$H NMR (300 MHz, DMSO-d6): δ(ppm) 8.88 (t, 1H), 7.31 (dd, 2H), 7.16 (t, 2H), 6.73 (wt, 1H), 4.2 (d, 2H), 4.10 (m, 2H) and 3.89 (m, 1H).

Example 9.1

2-(Acetylamino)-N-benzyl-3-(difluoromethoxy)propanamide

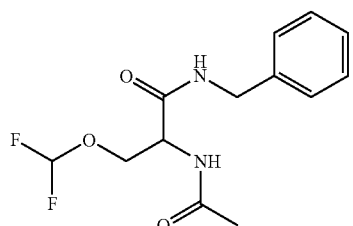

To a solution of 2-amino-N-benzyl-3-(difluoromethoxy) propanamide (195 mg, 0.798 mmol) and triethylamine (322 mg, 3.19 mmol) in THF (5 mL), acetic hydride (98.5 mg, 0.958 mmol) was added. The reaction mixture was stirred at room temperature for an hour, diluted with ethyl acetate and washed with water. The organic layer was concentrated with silica gel and purified by column chromatography, eluting with 50-100% ethyl acetate in hexanes. The product was triturated with diethyl ether to give 2-(acetylamino)-N-benzyl-3-(difluoromethoxy)propanamide (135 mg, 59%) as a white solid, MP: 173.3° C. $^1$H NMR (300 MHz, CDCl$_3$): δ (ppm) 7.25-7.39 (m, 5H), 6.68 (w, 1H), 6.42 (d, 1H), 6.24 (wt, 1H), 4.73 (m, 1H), 4.48 (d, 2H), 4.24 (dd, 1H), 4.01 (dd, 1H) and 2.05 (s, 3H).

Example 10.1

2-(Acetylamino)-3-(difluoromethoxy)-N-(4-fluorobenzyl)propanamide

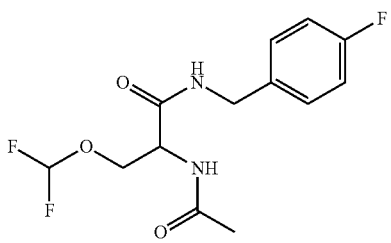 [SMILES: CC(=O)NC(COC(F)F)C(=O)NCc1ccc(F)cc1]

To a solution of 2-amino-3-difluoromethoxy-N-(4-fluorobenzyl)propionamide (200 mg, 0.762 mmol) and triethylamine (293 mg, 2.9 mmol) in THF (5 mL), acetic hydride (93 mg, 0.915 mmol) was added. The reaction mixture was stirred at room temperature for three hours, diluted with ethyl acetate, and washed with water. The organic layer was concentrated with silica gel and purified by column chromatography with 50-100% ethyl acetate in hexanes. The product was triturated with diethyl ether to give 2-(acetylamino)-N-benzyl-3-(difluoromethoxy)propanamide (140 mg, 60.3%) as a white solid, MP: 130.8° C. $^1$H NMR (300 MHz, CDCl$_3$): δ (ppm) 7.24 (dd, 2H), 7.03 (t, 2H), 6.73 (w, 1H), 6.41 (d, 1H), 6.24 (wt, 1H), 4.71 (m, 1H), 4.44 (d, 2H), 4.24 (dd, 1H), 4.01 (dd, 1H) and 2.05 (s, 3H).

Example 11.1

2-(Acetylamino)-N-(3,4-difluorobenzyl)-3-(difluoromethoxy)propanamide

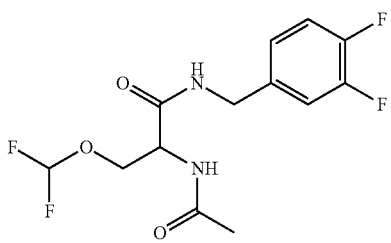 [SMILES: CC(=O)NC(COC(F)F)C(=O)NCc1ccc(F)c(F)c1]

2-dibenzylamino-N-(3,4-difluoro-benzyl)-3-difluoromethoxy-propionamide (298 mg, 0.645 mmol) was stirred with 10% Pd(OH)$_2$ (200 mg) in ethanol under H$_2$ overnight. The reaction mixture was filtered and concentrated. The residue was mixed with triethylamine (254 mg, 2.5 mmol) in dichloromethane (2 mL) and treated with acetic anhydride (85 μL) at room temperature for 2 hours. The reaction mixture was diluted with dichloromethane and washed with water. The organic layer was concentrated with silica gel and purified by column chromatography, eluting with 30-100% ethyl acetate in hexanes. The product was triturated with diethyl ether to give 2-amino-N-(3,4-difluorobenzyl)-3-(difluoromethoxy)propanamide (125 mg, 60%) as a white solid, MP: 146° C. $^1$H NMR (300 MHz, CDCl$_3$): δ(ppm) 6.92-7.16 (m, 4H), 6.47 (d, 1H), 6.25 (wt, 1H), 4.75 (m, 1H), 4.41 (m, 2H), 4.22 (dd, 1H), 4.02 (dd, 1H) and 2.05 (s, 3H).

Example 12.1

Benzyl (2R)-2-(dibenzylamino)-3-hydroxypropanoate

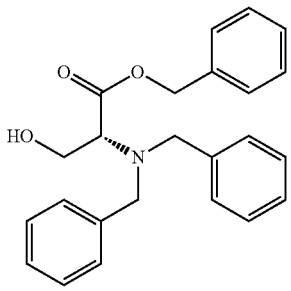 [SMILES: O=C(OCc1ccccc1)[C@@H](CO)N(Cc1ccccc1)Cc1ccccc1]

D-serine (10.5 g, 0.1 mol) was stirred with potassium carbonate (69 g, 0.5 mol), benzyl bromide (64.8 g, 0.375 mol) and water (10 mL) in acetonitrile (250 mL) at 55° C. for 24 hours. The reaction mixture was filtered and washed with ethyl acetate. The filtrate was concentrated with silica gel. The product was purified by column chromatography, eluting with 5-20% ethyl acetate in hexanes to give benzyl (2R)-2-(dibenzylamino)-3-hydroxypropanoate (33.36 g, 88%) as a pale-yellow sticky oil. $^1$H NMR (300 MHz, CDCl$_3$): δ (ppm) 7.20-7.44 (m, 15H), 5.27 (q, 2H), 3.91 (d, 2H), 3.80 (m, 2H), 3.67 (d, 2H), 3.63 (m, 1H) and 2.52 (dd, 1H).

Example 13.1

Benzyl (2R)-2-(dibenzylamino)-3-difluoromethoxypropionate

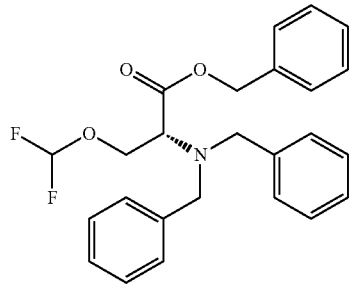 [SMILES: O=C(OCc1ccccc1)[C@@H](COC(F)F)N(Cc1ccccc1)Cc1ccccc1]

To a mixture of Benzyl (2R)-2-(dibenzylamino)-3-hydroxypropanoate (22.2 g, 59.2 mmol) and sodium sulfate (2.0 g, 14 mmol) in acetonitrile (200 mL) at 40° C., difluoro(fluorosulfonyl)acetic acid (10.5 g, 59.2 mmol) was added dropwise for 1.5 hrs. The reaction mixture was concentrated to dryness. The residue was mixed with ethyl acetate and silica gel, then concentrated again and purified by column chromatography, eluting with 1.5-2.5% ethyl acetate in hexanes to give benzyl (2R) 2-dibenzylamino-3-difluoromethoxy-propionate (3.375 g, 13.4%) as a colorless oil. $^1$H NMR (300 MHz, CDCl$_3$): δ (ppm) 7.20-7.40 (m, 15H), 6.17 (wt, 1H), 5.27 (q, 2H), 4.22 (dd, 1H), 4.10 (dd, 1H), 3.88 (d, 2H), 3.74 (t, 1H) and 3.65 (d, 2H).

Example 14.1

(2R)-2-Amino-3-(difluoromethoxy)propanoic acid

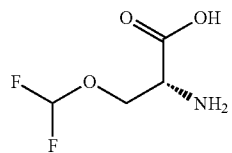

Benzyl (2R) 2-dibenzylamino-3-difluoromethoxy-propionate (3.1 g, 6.28 mmol) was stirred with Pd(OH)$_2$ in methanol under H$_2$ overnight. The reaction mixture was filtered and the filtrate concentrated to dryness, then triturated with diethyl ether to give (2R)-2-amino-3-(difluoromethoxy)propanoic acid (773 mg, 68.4%) as a white solid. $^1$H NMR (300 MHz, MeOD): δ (ppm) 6.49 (wt, 1H), 4.33 (dd, 1H), 4.22 (dd, 1H), and 3.88 (dd, 1H).

Example 15.1

(2R)-2-[(tert-Butoxycarbonyl)amino]-3-(difluoromethoxy)propanoic acid

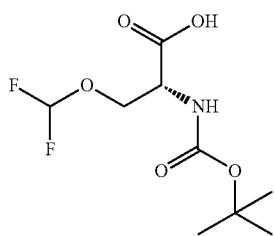

(2R)-2-Amino-3-(difluoromethoxy)propanoic acid (380 mg, 2.45 mmol) was stirred with sodium bicarbonate (411.6 mg. 4.90 mmol) and di-tert-butyl dicarbonate (902 mg, 3.68 mmol) in water (6 mL) and THF (2 mL) at room temperature overnight. The reaction mixture was diluted with water and extracted with ether to remove excess di-tert-butyl dicarbonate. The aqueous layer was acidified with 1N HCl to pH 2 and extracted with ethyl acetate, dried over magnesium sulphate and concentrated to give (2R)-2-[(tert-butoxycarbonyl) amino]-3-(difluoromethoxy)propanoic acid (515 mg, 82.3%) as a colorless sticky oil. $^1$H NMR (300 MHz, CDCl$_3$): δ(ppm) 6.23 (wt, 1H), 5.35 (d, 1H), 4.60 (m, 1H), 4.33 (m, 1H), 4.17 (m, 1H) and 1.51 (s, 9H).

Example 16.1 tert-Butyl {(1R)-2-(benzylamino)-1-[(difluoromethoxy)methyl]-2-oxoethyl}carbamate

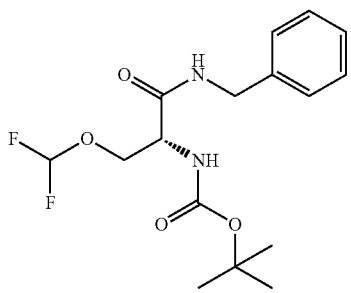 [SMILES: CC(C)(C)OC(=O)N[C@H](COC(F)F)C(=O)NCc1ccccc1]

To a solution of (2R)-2-[(tert-butoxycarbonyl)amino]-3-(difluoromethoxy)propanoic acid (510 mg, 2.0 mmol) and triethylamine (607.1 mg, 6 mmol) in THF (10 mL) at −78° C., isobutyl chloroformate (348 mg, 2.55 mmol) was added dropwise. After 30 minutes, benzylamine (321.5 mg, 3.0 mmol) was added and the reaction mixture allowed to warm up to room temperature. The mixture then was diluted with ethyl acetate and washed with water, 0.5N HCl and Brine. The organic layer was dried over magnesium sulphate, concentrated, and triturated with ether-hexanes (1:3) to give tert-butyl {(1R)-2-(benzylamino)-1-[(difluoromethoxy)methyl]-2-oxoethyl}carbamate (345 mg, 50%) as a white solid. $^1$H NMR (300 MHz, CDCl$_3$): δ(ppm) 7.40-7.80 (m, 5H), 6.60 (t, 1H), 6.22 (wt, 1H), 5.25 (w, 1H), 4.32-4.55 (m, 4H), 4.05 (dd, 1H) and 1.48 (s, 9H).

Example 17.1 tert-Butyl {(1R)-1-[(difluoromethoxy)methyl]-2-[(4-fluorobenzyl)amino]-2-oxoethyl}carbamate

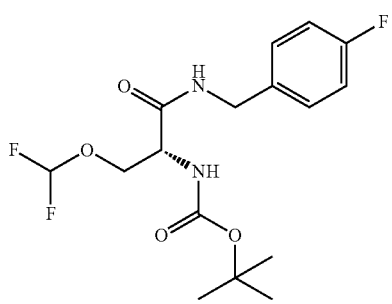 [SMILES: CC(C)(C)OC(=O)N[C@H](COC(F)F)C(=O)NCc1ccc(F)cc1]

To a solution of (2R)-2-[(tert-butoxycarbonyl)amino]-3-(difluoromethoxy)propanoic acid (780 mg, 3.05 mmol) and triethylamine (924 mg, 9.15 mmol) in THF (15 mL) at −78° C., isobutyl chloroformate (417.7 mg, 3.05 mmol) was added dropwise. After 30 minutes, (4-fluorobenzyl)amine (458 mg, 3.0 mmol) was added and the reaction mixture was allowed to warm up to room temperature. The mixture was then diluted with ethyl acetate and washed with water, 0.5N HCl and Brine. The organic layer was dried over magnesium sulphate, concentrated, and triturated with hexanes (1:3) to give tert-butyl {(1R)-1-[(difluoromethoxy)methyl]-2-[(4-fluorobenzyl)amino]-2-oxoethyl}carbamate (870 mg, 78.7%) as a white solid. $^1$H NMR (300 MHz, CDCl$_3$): δ(ppm) 7.23 (dd, 2H), 7.03 (t, 2H), 6.60 (b, 1H), 6.23 (wt, 1H), 5.24 (w, 1H), 4.3-4.51 (m, 4H), 4.02 (dd, 1H) and 1.45 (s, 9H).

Example 18.1 tert-butyl {(1R)-2-[(4-chlorobenzyl)amino]-1-[(difluoromethoxy)methyl]-2-oxoethyl}carbamate

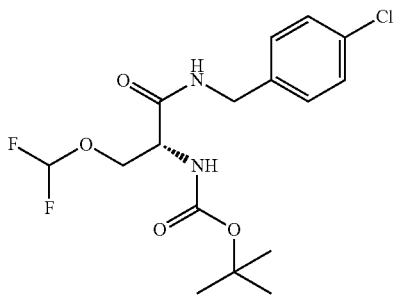 [SMILES: CC(C)(C)OC(=O)N[C@H](COC(F)F)C(=O)NCc1ccc(Cl)cc1]

To a solution of (2R)-2-Amino-3-(difluoromethoxy)propanoic acid (500 mg, 1.96 mmol) in THF (15 mL) at −78° C., 4-methylmorpholine (198 mg, 1.96 mmol) followed by isobutyl chloroformate (272 mg, 1.96 mmol) were added dropwise. (4-Chlorobenzyl)amine (332 mg, 2.35 mmol) was then added and the reaction mixture was allowed to warm up to room temperature. The mixture was then diluted with ethyl acetate and washed with water and brine. The organic layer was dried over magnesium sulphate, concentrated, and purified by column chromatography to yield tert-butyl {(1R)-2-[(4-chlorobenzyl)amino]-1-[(difluoromethoxy)methyl]-2-oxoethyl}carbamate.

(652 mg, 88%). $^1$H NMR (300 MHz, CDCl$_3$): δ(ppm) 7.36 (d, 2H), 7.20 (d, 2H), 6.64 (broad, 1H), 6.23 (wt, 1H), 5.24 (broad, 1H), 4.50 (d, 2H), 4.41 (broad, 1H), 4.32 (m, 1H), 4.03 (m, 1H), 1.45 (s, 9H).

In a similar manner the following compounds were synthesized:

| Example | Structure | Name | Yield |
|---|---|---|---|
| 18.2 | 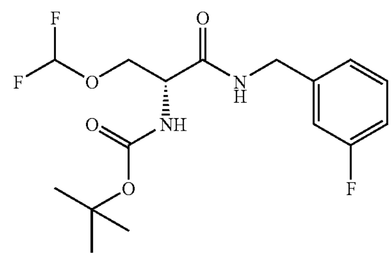 [SMILES: CC(C)(C)OC(=O)N[C@H](COC(F)F)C(=O)NCc1cccc(F)c1] | tert-butyl {(1R)-1-[(difluoromethoxy)methyl]-2-[(3-fluorobenzyl amino]-2-oxoethyl}carbamate | 623 mg, 88% yield |
| NMR | $^1$H NMR (300 MHz, CDCl$_3$): δ (ppm) 7.32 (m, 1H), 7.00 (m, 3H), 6.65 (broad, 1H), 6.24 (wt, 1H), 5.23 (broad, 1H), 4.49 (broad, 2H), 4.43 (broad, 1H), 4.35 (m, 1H), 4.05 (m, 1H), 1..46 (s, 9H) | | |
| 18.3 | 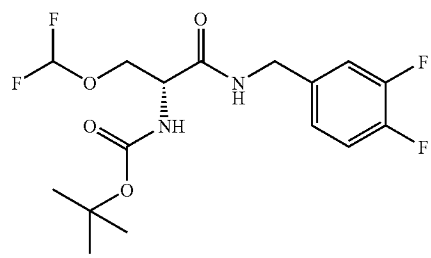 [SMILES: CC(C)(C)OC(=O)N[C@H](COC(F)F)C(=O)NCc1ccc(F)c(F)c1] | tert-butyl {(1R)-1-[(difluoromethoxy)methyl]-2-[(3,4-difluorobenzyl)amino]-2-oxoethyl}carbamate | 514 mg, 86% yield |
| NMR | $^1$H NMR (300 MHz, CDCl$_3$): δ (ppm) 7.16 (m, 2H), 7.00 (broad, 1H), 6.67 (broad, 1H), 6.24 (wt, 1H), 5.22 (broad, 1H), 4.46 (broad, 2H), 4.40 (broad, 1H), 4.34 (m, 1H), 4.03 (m, 1H), 1.46 (s, 9H) | | |
| 18.4 | 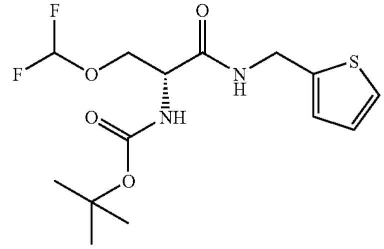 [SMILES: CC(C)(C)OC(=O)N[C@H](COC(F)F)C(=O)NCc1cccs1] | Tert-butyl {(1R)-1-[(difluoromethoxy)methyl]-2-oxo-2-[(2-thienylmethyl)amino]ethyl}carbamate | 559 mg, 82% yield |
| NMR | $^1$H NMR (300 MHz, CDCl$_3$): δ (ppm) 7.23 (d, 1H), 6.69 (m, 2H), 6.62 (broad, 1H), 6.23 (wt, 1H), 5.22 (broad, 1H), 6.52 (broad, 1H), 4.40 (broad, 1H), 4.32 (m, 1H), 4.02 (m, 1H), 1.45 (s, 9H) | | |

| Example | Structure | Name | Yield |
|---|---|---|---|
| 18.5 | 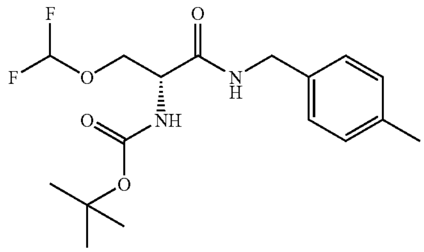 [SMILES: Cc1ccc(CNC(=O)[C@@H](COC(F)F)NC(=O)OC(C)(C)C)cc1] | tert-butyl {(1R)-1-[(difluoromethoxy)methyl]-2-[(4-methylbenzyl)amino]-2-oxoethyl}carbamate | 528 mg, 98% yield |
| NMR | $^1$H NMR (300 MHz, CDCl$_3$): δ (ppm) 7.18 (s, 4H), 6.51 (broad, 1H), 6.24 (wt, 1H), 5.21 (broad, 1H), 4.45 (broad, 2H), 4.40 (broad, 1H), 4.33 (m, 2H), 4.02 (m, 1H), 2.34 (s, 3H), 1.45 (s, 9H) | | |
| 18.6 | 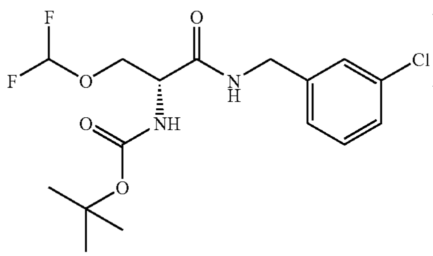 | tert-butyl {(1R)-2-[(3-chlorobenzyl)amino]-1-[(difluoromethoxy)methyl]-2-oxoethyl}carbamate | 354 mg, 95% yield |
| NMR | $^1$H NMR (300 MHz, CDCl$_3$): δ (ppm). 7.26 (m, 3H), 7.15 (m, 1H) < 6.65 (broad, 1H), 6.26 (wt, 1H), 5.21 (broad, 1H), 4.48 (broad t, 2H), 4.42 (broad, 1H), 4.35 (m, 1H), 4.04 (m, 1H), 1.46 (s, 9H) | | |
| 18.7 | 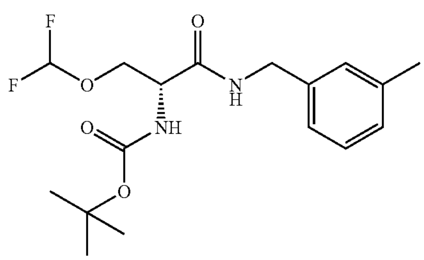 [SMILES: Cc1cccc(CNC(=O)[C@@H](COC(F)F)NC(=O)OC(C)(C)C)c1] | tert-butyl {(1R)-2-[(3-methylbenzyl)amino]-1-[(difluoromethoxy)methyl]-2-oxoethyl}carbamate | 339 mg, 97% yield |
| NMR | $^1$H NMR (300 MHz, CDCl$_3$): δ (ppm). 7.23 (t, 1H), 7.08 (t, 3H), 6.57 (broad, 1H), 6.23 (wt, 1H), 5.27 (broad, 1H), 4.44 (d, 2H), 4.41 (broad, 1H), 4.32 (m, 1H), 4.03 (m, 1H), 2.34 (s, 3H), 1.45 (s, 9H) | | |
| 18.8 | 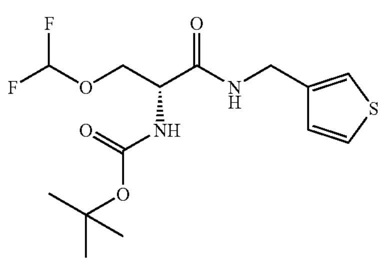 [SMILES: CC(C)(C)OC(=O)N[C@H](COC(F)F)C(=O)NCc1ccsc1] | tert-butyl {(1R)-1-[(difluoromethoxy)methyl]-2-oxo-2-[(3-thienylmethyl)amino]ethyl}carbamate | 330 mg, 96% yield |
| NMR | $^1$H NMR (300 MHz, CDCl$_3$): δ (ppm) 7.31 (m, 1H), 7.15 (s, 1H), 7.01 (d, 1H), 6.56 (broad, 1H), 6.24 (wt, 1H), 5.21 (broad, 1H), 4.49 (d, 1H), 4.40 (broad, 1H), 4.33 (m, 1H), 4.03 (m, 1H), 1.46 (s, 9H) | | |

Example 19.1

(2R)-2-(Acetylamino)-N-benzyl-3-(difluoromethoxy)propanamide

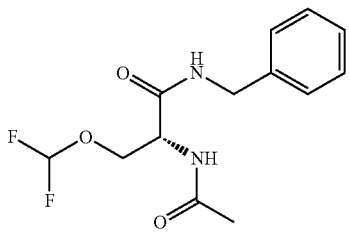 [SMILES: CC(=O)N[C@H](COC(F)F)C(=O)NCc1ccccc1]

Method A:

Tert-Butyl {(1R)-2-(benzylamino)-1-[(difluoromethoxy)methyl]-2-oxoethyl}carbamate (340 mg, 0.987 mmol) was stirred with trifluoroacetic acid (2.25 mL) and dichloromethane (2.5 mL) in an ice bath for an hour. The reaction mixture was concentrated, stirred with acetic anhydride-pyridine (1:1, 5.8 mL) at room temperature for 30 minutes and then diluted with ethyl acetate, washed with saturated sodium bicarbonate, brine, 0.5N HCl and brine again. The organic layer was dried, concentrated, and triturated with diethyl ether to give (2R)-2-(acetylamino)-N-benzyl-3-(difluoromethoxy)propanamide (230.5 mg, 77.2%) as a white solid. Mp: 186.9° C. $^1$H NMR (300 MHz, DMSO-d6): δ (ppm) 8.60 (t, 1H), 8.30 (d, 1H), 7.28-7.45 (m, 5H), 6.67 (wt, 1H), 4.58 (m, 1H), 4.40 (d, 2H), 3.98 (d, 2H) and 1.88 (s, 3H).

Method B:

To a solution of (2R)-2-[(tert-butoxycarbonyl)amino]-3-(difluoromethoxy)propanoic acid (197 mg, 1.0 mmol) and triethylamine (303 mg, 3 mmol) in THF (10 mL) at −78° C., isobutyl chloroformate (174 mg, 1.28 mmol) was added dropwise. After 30 minutes, benzylamine (161 mg, 1.5 mmol) was added and the reaction mixture was allowed to warm up to room temperature. The mixture then was diluted with ethyl acetate and washed with water, 0.5N HCl and Brine. The organic layer was dried over magnesium sulphate, concentrated, and triturated with ether-hexanes (1:3) to give (2R)-2-(acetylamino)-N-benzyl-3-(difluoromethoxy)propanamide (48 mg, 16.7%) as a white solid. $^1$H NMR (300 MHz, CDCl$_3$): δ(ppm) 7.25-7.39 (m, 5H), 6.68 (w, 1H), 6.42 (d, 1H), 6.24 (wt, 1H), 4.73 (m, 1H), 4.48 (d, 2H), 4.24 (dd, 1H), 4.01 (dd, 1H) and 2.05 (s, 3H).

Example 20.1

(2R)-2-(Acetylamino)-3-(difluoromethoxy)-N-(4-fluorobenzyl)propanamide

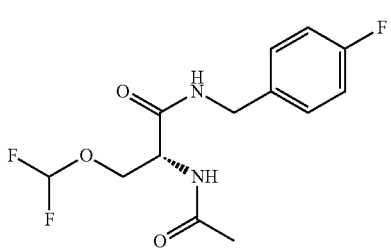 [SMILES: CC(=O)N[C@H](COC(F)F)C(=O)NCc1ccc(F)cc1]

Tert-Butyl {(1R)-1-[(difluoromethoxy)methyl]-2-[(4-fluorobenzyl)amino]-2-oxoethyl}carbamate (400 mg, 1.1 mmol) was stirred with trifluoroacetic acid (1.5 mL) and dichloromethane (2.5 mL) in an ice bath for an hour. The reaction mixture was concentrated, mixed with acetic anhydride-pyridine (1:1, 6 mL) at room temperature for 30 minutes and then diluted with ethyl acetate, washed with saturated sodium bicarbonate, brine, 0.5N HCl and brine again. The organic layer was dried, concentrated, and triturated with diethyl ether to give (2R)-2-(acetylamino)-3-(difluoromethoxy)-N-(4-fluorobenzyl)propanamide (220 mg, 65.7%) as a white solid. Mp: 162.7° C. $^1$H NMR (300 MHz, CDCl$_3$): δ (ppm) 7.24 (dd, 2H), 7.03 (t, 2H), 6.78 (w, 1H), 6.35 (d, 1H), 6.24 (wt, 1H), 4.71 (m, 1H), 4.44 (d, 2H), 4.24 (dd, 1H), 4.01 (dd, 1H) and 2.05 (s, 3H).

Example 21.1

(2R)-2-(Acetylamino)-3-(difluoromethoxy)propanoic acid

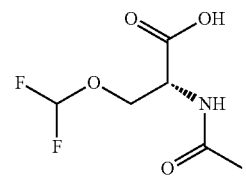

(2R)-2-Amino-3-(difluoromethoxy)propanoic acid (680 mg, 4.39 mmol) was mixed with sodium bicarbonate (738 mg. 8.78 mmol) and acetic anhydride (491 mg, 4.82 mmol) in water (10 mL) and dioxane (10 mL) at 0° C. to room temperature overnight. The reaction mixture was acidified with 1N HCl to pH 2, concentrated and extracted with ethyl acetate, and concentrated again to give (2R)-2-(Acetylamino)-3-(difluoromethoxy)propanoic acid (580 mg, 82.3%) as a colorless sticky oil. $^1$H NMR (300 MHz, CDCl$_3$): δ (ppm) 6.40 (d, 1H), 6.24 (wt, 1H), 4.88 (m, 1H), 4.36 (dd, 1H), 4.22 (dd, 1H), 2.12 (s, 3H).

Example 22.1

(2R)—N-benzyl-3-(difluoromethoxy)-2-[(methylsulfonyl)amino]propanamide

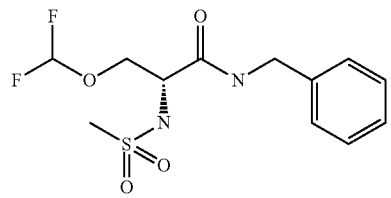 [SMILES: CS(=O)(=O)N[C@H](COC(F)F)C(=O)NCc1ccccc1]

A solution of (2R)-2-amino-N-benzyl-3-(difluoromethoxy)propanamide (113 mg, 0.46 mmol) in ethyl acetate was cooled in an ice bath. To the cooled solution was added triethylamine (139 mg, 1.38 mmol) followed by methanesulfonylchloride (63 mg, 0.55 mmol). The reaction mixture was stirred for 15 minutes and then quenched with water, extracted with ethyl acetate and washed with brine. The organic layer was dried, concentrated and triturated with diethyl ether to give the product (33 mg, 22%) as a white solid. $^1$H NMR (300 MHz, CDCl$_3$): δ (ppm) 7.31 (m, 5H), 6.73 (br, 1H), 6.24 (t, 1H), 5.21 (d, 1H), 4.48 (d, 2H), 4.21 (m, 3H), 3.01 (s, 3H)

In a similar manner the following compound was prepared:

| Example | Structure | Name | Yield |
|---|---|---|---|
| 22.2 | 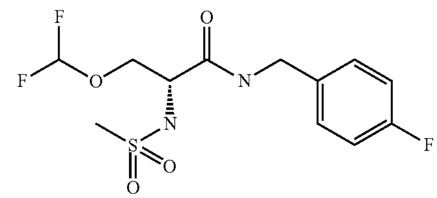 [SMILES: CS(=O)(=O)N[C@H](COC(F)F)C(=O)NCc1ccc(F)cc1] | (2R)-3-(difluoromethoxy)-N-(4-fluorobenzyl)-2-[(methylsulfonyl)amino]propanamide | White solid, 96 mg, 30% |
| NMR | $^1$H NMR (300 MHz, CDCl$_3$): δ (ppm) 7.23 (m, 2H), 7.03 (dd, 2H), 6.76 (br, 1H), 6.22 (t, 1H), 5.16 (dd, 1H), 4.45 (dd, 2H), 4.12 (m, 3H), 2.99 (s, 3H) | | |

Example 23.1

(2R)-2-(acetylamino)-N-(4-chlorobenzyl)-3-(difluoromethoxy)propanamide

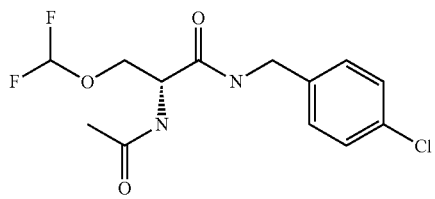 [SMILES: CC(=O)N[C@H](COC(F)F)C(=O)NCc1ccc(Cl)cc1]

A solution of tert-butyl {(1R)-2-[(4-chlorobenzyl)amino]-1-[(difluoromethoxy)methyl]-2-oxoethyl}carbamate (652 mg, 1.72 mmol) in dichloromethane (7 mL) was cooled in an ice-water bath and trifluoroacetic acid (7 mL) was added and stirred for 30 minutes. The mixture was concentrated and diluted with water and basified, extracting with ethyl acetate. The organic extracts were washed with brine, dried over magnesium sulphate and concentrated to yield the product (444 mg, 92%), which was dissolved in ethyl acetate and cooled in an ice bath. To the cooled solution was added triethylamine (242 mg, 2.4 mmol) followed by acetyl chloride (118 mg, 1.2 mmol). The reaction mixture was stirred for 15 minutes and then quenched with water, extracted with ethyl acetate and washed with brine. The organic layer was dried, concentrated and triturated with diethyl ether to give (2R)-2-(acetylamino)-N-(4-chlorobenzyl)-3-(difluoromethoxy)propanamide (446 mg, 87%). $^1$H NMR (300 MHz, CDCl$_3$): δ(ppm) 8.64 (t, 1H), 8.26 (d, 1H), 7.41 (d, 2H), 7.22 (d, 2H), 6.42 (t, 1H), 4.58 (q, 1H), 4.27 (d, 2H), 3.98 (d, 2H), 1.88 (s, 3H).

In a similar manner the following compounds were prepared:

| Example | Structure | Name | Yield |
|---|---|---|---|
| 23.2 | 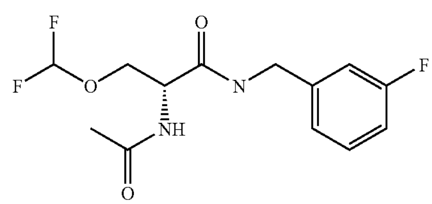 [SMILES: CC(=O)N[C@H](COC(F)F)C(=O)NCc1cccc(F)c1] | (2R)-2-(acetylamino)-3-(difluoromethoxy)-N-(3-fluorobenzyl)propanamide | White solid, 422 mg, 86% |
| NMR | $^1$H NMR (300 MHz, CDCl$_3$): 8.64 (t, 1H), 8.27 (d, 1H), 7.34 (m, 1H), 7.03 (m, 3H), 6.66 (wt, 1H), 4.56 (m, 1H), 4.32 (d, 2H), 4.00 (d, 2H), 1.89 (s, 3H) | | |
| 23.3 | 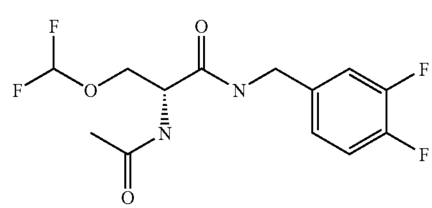 [SMILES: CC(=O)N[C@H](COC(F)F)C(=O)NCc1ccc(F)c(F)c1] | (2R)-2-(acetylamino)-N-(3,4-difluorobenzyl)-3-(difluoromethoxy)propanamide | White solid, 320 mg, 76% |
| NMR | $^1$H NMR (300 MHz, DMSO): δ (ppm) 8.64 (t, 1H), 8.27 (d, 1H), 7.32 (m, 2H), 7.08 (br, 1H), 6.66 (t, 1H), 4.56 (q, 1H), 4.27 (d, 2H), 3.99 (d, 2H), 1.89 (s, 3H) | | |

| Example | Structure | Name | Yield |
| --- | --- | --- | --- |
| 23.4 | 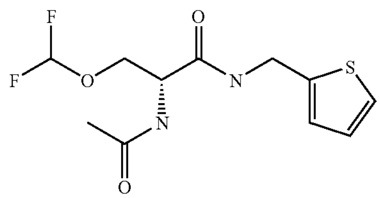 [SMILES: CC(=O)N[C@H](COC(F)F)C(=O)NCc1cccs1] | (2R)-2-(acetylamino)-3-(difluoromethoxy)-N-(2-thienylmethyl)propanamide | White solid, 376 mg, 92% |
| NMR | $^1$H NMR (300 MHz, DMSO): δ (ppm) 8.69 (t, 1H), 8.24 (d, 1H), 7.38 (m, 1H), 6.94 (m, 2H), 6.64 (t, 1H), 4.55 (q, 1H), 4.43 (d, 2H), 3.96 (m, 2H), 1.87 (s, 3H) | | |
| 23.5 | 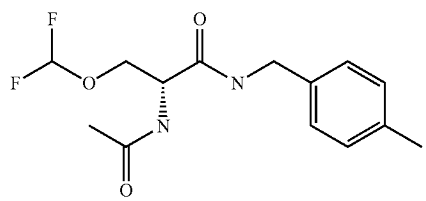 [SMILES: CC(=O)N[C@H](COC(F)F)C(=O)NCc1ccc(C)cc1] | (2R)-2-(acetylamino)-3-(difluoromethoxy)-N-(4-methylbenzyl)propanamide | White solid, 337 mg, 83% |
| NMR | $^1$H NMR (300 MHz, DMSO): δ (ppm) 8.56 (t, 1H), 8.24 (d, 1H), 7.11 (m, 4H), 6.66 (t, 1H), 4.57 (q, 1H), 4.23 (d, 2H), 3.97 (d, 2H), 2.26 (s, 3H), 1.88 (s, 3H) | | |
| 23.6 | 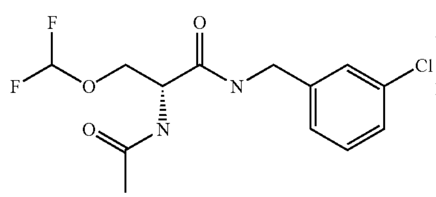 | (2R)-2-(acetylamino)-N-(3-chlorobenzyl)-3-(difluoro-methoxy)propanamide | White solid, 240 mg, 80% |
| NMR | $^1$H NMR (300 MHz, DMSO): δ (ppm) 8.64 (t, 1H), 8.27 (dd, 1H), 7.31 (m, 3H), 7.2 (dd, 1H), 6.66 (t, 1H), 4.57 (q, 1H), 4.29 (dd, 2H), 4.02 (dd, 2H), 1.89 (s, 3H) | | |
| 23.7 | 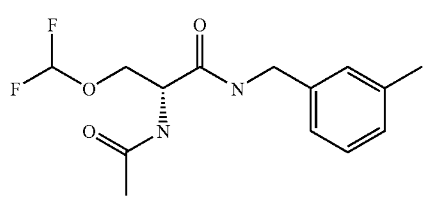 [SMILES: CC(=O)N[C@H](COC(F)F)C(=O)NCc1cccc(C)c1] | (2R)-2-(acetylamino)-3-(difluoromethoxy)-N-(3-methylbenzyl)propanamide | White solid, 212 mg, 74% |
| NMR | $^1$H NMR (300 MHz, DMSO): δ (ppm) 8.56 (t, 1H), 8.24 (d, 1H), 7.18 (t, 1H), 7.03 (m, 3H), 6.66 (t, 1H), 4.58 (q, 1H), 4.25 (d, 2H), 3.99 (d, 2H), 2.27 (s, 3H), 1.88 (s, 3H) | | |
| 23.8 | 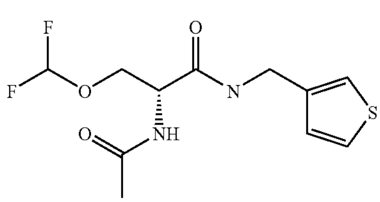 [SMILES: CC(=O)N[C@H](COC(F)F)C(=O)NCc1ccsc1] | (2R)-2-(acetylamino)-3-(difluoromethoxy)-N-(3-thienylmethyl)propanamide | White solid, 195 mg, 78% |
| NMR | $^1$H NMR (300 MHz, DMSO): δ (ppm) 8.55 (t, 1H), 8.23 (d, 1H), 7.46 (dd, 1H), 7.24 (d, 1H), 6.99 (d, 1H), 6.66 (t, 1H), 4.57 (q, 1H), 4.27 (d, 2H), 3.97 (d, 2H), 1.88 (s, 3H) | | |

Example 24.1

2-Acetylamino-N-benzyl-3-difluoromethoxy-propionamide

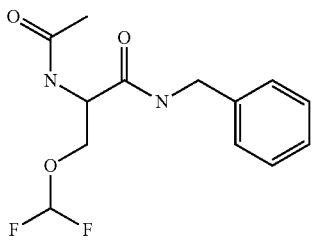 [SMILES: CC(=O)NC(COC(F)F)C(=O)NCc1ccccc1]

2-Amino-N-benzyl-3-difluoromethoxy-propionamide (195 mg, 0.80) was mixed with triethylamine (322 mg, 3.19 mmol) in THF (5 mL). Acetic anhydride (98.5 mg, 0.96 mmol) was then added and the reaction mixture was stirred for 1 hour. The mixture was then diluted with ethyl acetate and washed with water. The organic layer was dried and concentrated. The residue was purified by column chromatography using hexanes:ethyl acetate (50:50 to 0:100). The isolated product was triturated with diethyl ether to give 2-acetylamino-N-benzyl-3-difluoromethoxy-propionamide (135 mg, 59%) as a white solid. $^1$H NMR (300 MHz, CDCl$_3$): δ (ppm) 7.33 (m, 5H), 6.68 (br, 1H), 6.37 (br, 1H), 6.24 (t, 1H), 4.72 (q, 1H), 4.87 (d, 2H), 4.23 (dd, 1H), 4.01 (dd, 1H), 2.05 (s, 3H).

In a similar manner the following compounds were prepared:

Example 25.1

Conditioned Emotional Response Assay

Male, Sprague-Dawley rats of approximate body weight 350-450 g were placed on a restricted food diet (45 min free access per day) and trained over a 1-2 week period to press a lever for food reward (45 mg food pellet). Schedule requirements were gradually increased from a variable interval 5 s schedule (VI5) to a final variable interval 40 s schedule (VI40). Test session length was for a 40 min test period, and test sessions were run 5 days/week. Once stable response rates were attained, 2 periods of a 2 min light and tone cue (conditioning stimulus, CS) was introduced into the test session. The 2 min CS was terminated by a 0.5 s unavoidable footshock of 0.3-0.8 mA intensity (UCS). The first CS-UCS was at approximately 10 min (range 5-15 min) and the second CS-UCS pairing at approximately 30 min (range 25-35 min) within the test session. On drug test days, and occasional training days, footshock was not delivered. The number of lever presses recorded during the two 2 min CS periods (response A), and the number of lever presses recorded in the 2 min periods immediately prior to the two CS periods (response B) were measured and a suppression ratio (SR) was calculated according to the formula (A/A+B). Thus a SR of 0 reflects no responding during the CS periods, i.e. a complete suppression of lever pressing for food by the CS, and a SR of 0.5 reflects equivalent responding during both the CS and 2 min period prior to CS, i.e. no suppression of lever pressing for food by the CS. Thus in drug untreated animals, SR value was typically 0-0.1 and established anti-anxiety agents such as diazepam increased this value to 0.4-0.5 (for literature examples see Stanhope and Dourish (1996) Psychopharmacol. 128: 293-303; Mirza et al (2005) Psychopharmacol. 180:

| Example | Structure | Name | Yield |
|---------|-----------|------|-------|
| 24.2 | 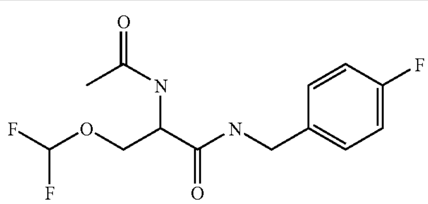 [SMILES: CC(=O)NC(COC(F)F)C(=O)NCc1ccc(F)cc1] | 2-Acetylamino-3-difluoromethoxy-N-(4-fluoro-benzyl)-propionamide | White solid, 140 mg, 60% |
| NMR | $^1$H NMR (300 MHz, CDCl$_3$): δ (ppm) 7.25 (m, 2H), 7.03 (t, 2H), 6.73 (br, 1H), 6.39 (br, 1H), 6.24 (t, 1H), 4.71 (q, 1H), 4.43 (dd, 2H), 4.25 (dd, 1H), 4.02 (dd, 1H), 2.05 (s, 3H) | | |
| 24.3 | 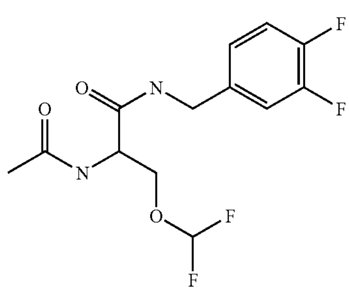 [SMILES: CC(=O)NC(COC(F)F)C(=O)NCc1ccc(F)c(F)c1] | 2-Acetylamino-N-(3,4-difluoro-benzyl)-3-difluoromethoxy-propionamide | White solid, 125 mg |
| NMR | $^1$H NMR (300 MHz, CDCl$_3$): δ (ppm) 7.11 (m, 4H), 6.5 (br, 1H), 6.24 (t, 1H), 4.75 (q, 1H), 4.42 (dd, 2H), 4.22 (dd, 1H), 3.49 (dd, 1H), 2.05 (s, 3H) | | |

159-168). In addition to SR, the total number of lever presses emitted by the animals over the 40 min test session was measured.

Drug testing was conducted according to a repeated measures design, with each animal receiving each dose of drug treatment or vehicle control in a balanced design. Typically drug testing was conducted on Tuesdays and Fridays, with the animals drug untreated but otherwise run for baseline purposes. In each experiment a standard dose of diazepam (2 mg/kg i.p) was included as a positive control.

Lacosamide((+)-(2R)-2-(acetylamino)-N-benzyl-3-methoxypropanamide) demonstrated efficacy in the CER assay by significantly increasing the SR value from doses 3-30 mg/kg i.p. The magnitude of this effect was equivalent to diazepam (2 mg/kg i.p). The (S)-enantiomer of Lacosamide was ineffective in this assay.

Compounds of Examples 19.1, 20.1, 23.1 were all similarly active in increasing the SR in a dose-related manner, and to a level equivalent to diazepam.

Summary of Data from the Conditioned Emotional Response Assay of Anxiety.

Data presented as the mean±SEM from at least 10 rats per experiment. *$p<0.05$ compared to vehicle pretreated controls.

| Compound | Dose | Suppression ratio (SR) | Total number lever press |
|---|---|---|---|
| Lacosamide | 0 | 0.08 ± 0.03 | 1068 ± 122 |
| | 3 | 0.16 ± 0.07 | 1166 ± 185 |
| | 10 | 0.18 ± 0.08 | 1121 ± 138 |
| | 30 | 0.36 ± 0.07* | 727 ± 123* |
| (S)-enantiomer of Lacosamide | 30 | 0.06 ± 0.03 | 1403 ± 158 |
| Diazepam | 2 | 0.32 ± 0.07* | 1239 ± 183 |
| Example 19.1 | 0 | 0.13 ± 0.04 | 957 ± 78 |
| | 3 | 0.16 ± 0.03 | 1169 ± 145 |
| | 10 | 0.15 ± 0.05 | 1093 ± 169 |
| | 30 | 0.38 ± 0.04* | 724 ± 135* |
| Diazepam | 2 | 0.39 ± 0.04* | 899 ± 146 |
| Example 20.1 | 0 | 0.11 ± 0.04 | 1150 ± 112 |
| | 3 | 0.17 ± 0.06 | 1188 ± 95 |
| | 10 | 0.28 ± 0.07* | 1170 ± 98 |
| | 20 | 0.33 ± 0.06* | 849 ± 78* |
| | 30 | 0.43 ± 0.05* | 587 ± 84* |
| Diazepam | 2 | 0.44 ± 0.03* | 1015 ± 155 |
| Example 23.1 | 0 | 0.04 ± 0.01 | 838 ± 83 |
| | 3 | 0.09 ± 0.04 | 1091 ± 169 |
| | 10 | 0.17 ± 0.04* | 1034 ± 131 |
| | 30 | 0.26 ± 0.04* | 578 ± 79* |
| Diazepam | 2 | 0.44 ± 0.03* | 1151 ± 138 |

Example 26.1

Marble Burying Assay

Male, experimentally naïve CD-1 mice of body weight range 25-35 g were used in these studies. Following a pretreatment with test drug or vehicle control the animals were singly placed within a Perspex chamber of dimension (48 cm×28 cm×20 cm; L×W×H) containing fresh sawdust bedding onto which 22 marbles were evenly spaced on the surface. After a 30 min period, the mice were removed and the number of marbles that were covered by at least ⅔rd by sawdust were counted as buried. Typically mice will bury a significant proportion of the marbles, probably to hide the potential threat posed by the marbles which represent a novel stimulus to the animal. A number of anti-anxiety drugs such as diazepam have been shown to reduce the number of marbles buried by mice at doses with no obvious effect on general motor function. One interpretation for this effect is that diazepam reduces the threat perceived to the animal by the close presence of the marbles (Broekkamp et al, 1986 Eur. J. Pharmacol. 126: 223-229; Nicolas et al, 2006 Eur. J. Pharmacol. 547; 106-115). In a separate group of sex, age and weight matched CD-1 mice, equivalent doses of test compound were evaluated on motor function using a fixed speed (16 r.p.m) rotorod assay. The best score from 3 attempts was recorded, with the maximum test duration of 60 s. Testing was conducted at 40 min post injection, i.e. approximate midpoint of the marble-burying assay.

Drug testing was run according to a between subjects design. Lacosamide demonstrated efficacy in the marble burying assay by significantly reducing the number of marbles buried compared to vehicle pretreated controls at oral doses of 3-30 mg/kg. The (S)-enantiomer of Lacosamide was ineffective in this assay.

Compounds of Examples 19.1, 20.1, 23.1 were all similarly active in decreasing marble burying in a dose-related manner. The standard anxiolytic drug diazepam also produced a similar profile in this test.

Summary of Data from the Mouse Marble Burying Assay of Anxiety.

Marble burying data presented as the mean±SEM from at least 8 mice per treatment. *$p<0.05$ compared to vehicle pretreated controls. Rotorod score is the median value from at least 4 mice per treatment (maximum score=60 s). All treatments were administered by the i.p or oral route.

| Compound | Dose | Number of marbles buried | Rotorod score (s) |
|---|---|---|---|
| Lacosamide | 0 | 17.4 ± 0.8 | 60 |
| | 3 | 16.8 ± 0.8 | 60 |
| | 10 | 18.0 ± 0.7 | 60 |
| | 30 | 12.4 ± 1.4* | 60 |
| Example 19.1 | 0 | 18.0 ± 0.8 | 60 |
| | 3 | 17.0 ± 1.1 | 60 |
| | 10 | 9.7 ± 2.3* | 60 |
| | 30 | 2.3 ± 2.0* | 13 |
| Example 20.1 | 0 | 15.9 ± 0.7 | 60 |
| | 3 | 15.0 ± 1.2 | 60 |
| | 10 | 14.9 ± 0.9 | 60 |
| | 30 | 10.3 ± 1.5* | 60 |
| Example 23.1 | 0 | 15.3 ± 1.0 | 60 |
| | 3 | 15.8 ± 0.8 | 60 |
| | 10 | 12.3 ± 1.2 | 60 |
| | 30 | 2.0 ± 0.7* | 60 |
| Diazepam | 0 | 13.1 ± 1.3 | 60 |
| | 0.3 | 12.6 ± 1.4 | 60 |
| | 1 | 9.4 ± 1.7 | 60 |
| | 2 | 2.2 ± 1.2* | — |
| | 3 | 2.0 ± 0.8* | 40 |

All publications, including but not limited to patents and patent applications, cited in this specification are herein incorporated by reference as if each individual publication were specifically and individually indicated to be incorporated by reference herein and as though fully set forth.

Modifications and improvements of the embodiments specifically disclosed herein are within the scope of the following claims. Without further elaboration, it is believed that one skilled in the area can, using the preceding description, utilize the present disclosure to its fullest extent. Therefore the Examples herein are to be construed as merely illustrative and not a limitation of the scope of the present invention as claimed hereinafter. The embodiments disclosed, in which an exclusive property or privilege is claimed are defined as follows.

It will be obvious to those having skill in the art that many changes may be made to the details of the above-described embodiments. The scope of the present invention should, therefore, be determined only by the following claims.

We claim:

1. A method of treating an anxiety disorder comprising administering to a patient a therapeutically effective amount of a compound of Formula I or a salt thereof:

Formula I wherein:
- A is chosen from: aryl or heteroaryl, A being optionally substituted with up to 5 independently-selected groups $R^8$;
- $R^1$ is chosen from: alkyl or haloalkyl;
- $R^2$ is chosen from: H, $C(O)R^6$, $C(O)OR^6$, $SO_2R^6$ or $C(O)NR^6R^7$;
- $R^3$, $R^4$ and $R^5$ are independently chosen from: H or alkyl;
- $R^6$ and $R^7$ are independently chosen from: H or alkyl; and
- $R^8$ is chosen from: OH, CN, halo, alkyl, alkoxy, haloalkyl, haloalkoxy, $C(O)R^6$, $C(O)OR^6$, $SO_2R^6$ or $C(O)NR^6R^7$, and wherein the anxiety disorder is chosen from: generalized anxiety disorder (GAD) or social phobias.

2. The method of claim 1, wherein the compound is an R enantiomer having the following chemical formula:

or a salt thereof.

3. The method of claim 1, wherein:
- $R^2$ is chosen from: H, $C(O)R^6$, $C(O)OR^6$, or $SO_2R^6$;
- $R^3$, $R^4$ and $R^5$ are each H;
- $R^6$ is alkyl; and
- $R^8$ is chosen from: halo or alkyl.

4. The method of claim 3, wherein the compound is an R enantiomer having the following chemical formula:

or a salt thereof.

5. The method of claim 4, wherein:
- $R^1$ is chosen from: methyl or $CHF_2$; and
- $R^6$ is chosen from: methyl or tert-butyl.

6. The method of claim 4, wherein:
- A is aryl, optionally substituted with up to 5 independently-selected groups $R^8$;
- $R^2$ is $C(O)R^6$; and
- $R^8$ is halo.

7. The method of claim 6, wherein:
- $R^1$ is haloalkyl; and
- $R^6$ is methyl.

8. The method of claim 1, wherein the compound is or a salt thereof.

9. The method of claim 1, wherein the compound is chosen from:

or a salt thereof.

* * * * *

UNITED STATES PATENT AND TRADEMARK OFFICE
CERTIFICATE OF CORRECTION

| | | |
|---|---|---|
| PATENT NO. | : 8,450,336 B2 | Page 1 of 1 |
| APPLICATION NO. | : 12/519041 | |
| DATED | : May 28, 2013 | |
| INVENTOR(S) | : Higgins et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 573 days.

Signed and Sealed this
Sixteenth Day of December, 2014

Michelle K. Lee
*Deputy Director of the United States Patent and Trademark Office*